US009279153B2

(12) United States Patent
Huber

(10) Patent No.: US 9,279,153 B2
(45) **Date of Patent: *Mar. 8, 2016**

(54) ULTRAFAST SEQUENCING OF BIOLOGICAL POLYMERS USING A LABELED NANOPORE

(71) Applicant: Quantapore, Inc., Menlo Park, CA (US)

(72) Inventor: Martin Huber, Menlo Park, CA (US)

(73) Assignee: Quantapore, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/285,474

(22) Filed: May 22, 2014

(65) Prior Publication Data

US 2014/0255935 A1 Sep. 11, 2014

Related U.S. Application Data

(63) Continuation of application No. 13/426,515, filed on Mar. 21, 2012, now Pat. No. 8,771,491, which is a continuation of application No. PCT/US2010/034809, filed on May 13, 2010.

(60) Provisional application No. 61/277,939, filed on Sep. 30, 2009.

(51) Int. Cl.
*G01N 27/327* (2006.01)
*G01N 27/453* (2006.01)
(Continued)

(52) U.S. Cl.
CPC ........ *C12Q 1/6869* (2013.01); *G01N 33/48721* (2013.01)

(58) Field of Classification Search
CPC ................................................ G01N 33/48721
See application file for complete search history.

(56) References Cited

U.S. PATENT DOCUMENTS

| | | | |
|---|---|---|---|
| 4,161,690 | A | 7/1979 | Feier |
| 5,131,755 | A | 7/1992 | Chadwick et al. |
| 5,387,926 | A | 2/1995 | Bellan |

(Continued)

FOREIGN PATENT DOCUMENTS

| | | |
|---|---|---|
| CN | 1403817 | 3/2003 |
| CN | 201302544 | 9/2009 |

(Continued)

OTHER PUBLICATIONS

Aksimentiev, a. et al., "Microscopic Kinetics of DNA Translocation through Synthetic Nanopores," *Biophysical Journal*,vol. 87, pp. 2086-2097, Sep. 2004.

(Continued)

*Primary Examiner* — Alexander Noguerola
(74) *Attorney, Agent, or Firm* — Levine Bagade Han LLP

(57) ABSTRACT

Methods and systems for sequencing a biological molecule or polymer, e.g., a nucleic acid, are provided. One or more donor labels, which are attached to a pore or nanopore, may be illuminated or otherwise excited. A polymer having a monomer labeled with one or more acceptor labels, may be translocated through the pore. Either before, after or while the labeled monomer of the polymer passes through, exits or enters the pore, energy may be transferred from the excited donor label to the acceptor label of the monomer. As a result of the energy transfer, the acceptor label emits energy, and the emitted energy is detected in order to identify the labeled monomer of the translocated polymer and to thereby sequence the polymer.

17 Claims, 9 Drawing Sheets

(51) Int. Cl.
*C12Q 1/68* (2006.01)
*G01N 33/487* (2006.01)

(56) References Cited

U.S. PATENT DOCUMENTS 5,405,747 A 4/1995 Jett et al.
5,470,705 A 11/1995 Grossman et al.
5,580,732 A 12/1996 Grossman et al.
5,624,800 A 4/1997 Grossman et al.
5,795,782 A 8/1998 Church et al.
5,798,042 A 8/1998 Chu et al.
5,821,058 A 10/1998 Smith et al.
5,989,871 A 11/1999 Grossman et al.
6,015,714 A 1/2000 Baldarelli et al.
6,210,896 B1 4/2001 Chan
6,211,955 B1 4/2001 Basiji et al.
6,249,341 B1 6/2001 Basiji et al.
6,251,303 B1 6/2001 Bawendi et al.
6,252,303 B1 6/2001 Huang
6,263,286 B1 7/2001 Gilmanshin et al.
6,267,872 B1 7/2001 Akeson et al.
6,325,968 B1 12/2001 Fricker et al.
6,335,420 B1 1/2002 Bruening et al.
6,335,440 B1 1/2002 Lee et al.
6,355,420 B1 3/2002 Chan
6,362,002 B1 3/2002 Denison et al.
6,413,792 B1 7/2002 Sauer et al.
6,426,231 B1 7/2002 Bayley et al.
6,428,959 B1 8/2002 Deamer
6,429,897 B2 8/2002 Derndinger et al.
6,447,724 B1 9/2002 Jensen et al.
6,464,842 B1 10/2002 Golovchenko et al.
6,465,193 B2 10/2002 Akeson et al.
6,473,176 B2 10/2002 Basiji et al.
6,498,010 B1 12/2002 Fitzgerald et al.
6,503,757 B1 1/2003 Chow
6,504,943 B1 1/2003 Sweatt et al.
6,511,802 B1 1/2003 Albrecht et al.
6,528,258 B1 3/2003 Russell
6,537,755 B1 3/2003 Drmanac
6,583,865 B2 6/2003 Basiji et al.
6,608,680 B2 8/2003 Basiji et al.
6,608,682 B2 8/2003 Ortyn et al.
6,616,895 B2 9/2003 Dugas et al.
6,617,113 B2 9/2003 Deamer
6,618,140 B2 9/2003 Frost et al.
6,618,679 B2 9/2003 Loehrlein et al.
6,627,067 B1 9/2003 Branton et al.
6,671,044 B2 12/2003 Ortyn et al.
6,673,615 B2 1/2004 Denison et al.
6,706,203 B2 3/2004 Barth et al.
6,723,515 B2 4/2004 Barron
6,743,905 B2 6/2004 Woo et al.
6,746,594 B2 6/2004 Akeson et al.
6,752,914 B1 6/2004 Hassard
6,756,204 B2 6/2004 Grossman et al.
6,758,961 B1 7/2004 Vogel et al.
6,772,070 B2 8/2004 Gilmanshin et al.
6,790,671 B1 9/2004 Austin et al.
6,821,726 B1 11/2004 Dahm et al.
6,824,659 B2 11/2004 Bayley et al.
6,830,670 B1 12/2004 Viovy et al.
6,855,551 B2 2/2005 Bawendi et al.
6,856,390 B2 2/2005 Nordman et al.
6,906,749 B1 6/2005 Fox
6,916,665 B2 7/2005 Bayley et al.
6,936,433 B2 8/2005 Akeson et al.
6,947,128 B2 9/2005 Basiji et al.
6,952,651 B2 10/2005 Su
6,975,400 B2 12/2005 Ortyn et al.
6,982,146 B1 1/2006 Schneider et al.
6,998,251 B2 2/2006 Guttman et al.
7,001,792 B2 2/2006 Sauer et al.
7,005,264 B2 2/2006 Su et al.
7,008,547 B2 3/2006 Chen et al.
7,049,104 B2 5/2006 Kambara et al.
7,052,847 B2 5/2006 Korlach et al.
7,056,661 B2 6/2006 Korlach et al.
7,056,676 B2 6/2006 Korlach et al.
7,060,507 B2 6/2006 Akeson et al.
7,074,569 B2 7/2006 Woo et al.
7,129,050 B2 10/2006 Grossman et al.
7,189,503 B2 3/2007 Akeson et al.
7,201,836 B2 4/2007 Vogel et al.
7,235,184 B2 6/2007 Dugas et al.
7,235,361 B2 6/2007 Bawendi et al.
7,238,485 B2 7/2007 Akeson et al.
7,244,349 B2 7/2007 Vogel et al.
7,248,771 B2 7/2007 Schmidt et al.
7,250,115 B2 7/2007 Barth
7,271,896 B2 9/2007 Chan et al.
7,279,337 B2 10/2007 Zhu
7,280,207 B2 10/2007 Oldham et al.
7,285,010 B2 10/2007 Hatakeyama et al.
7,364,851 B2 4/2008 Berlin et al.
7,371,533 B2 5/2008 Slater et al.
7,381,315 B2 6/2008 Grossman et al.
7,387,715 B2 6/2008 Vogel et al.
7,390,457 B2 6/2008 Schembri
7,397,232 B2 7/2008 Hu et al.
7,410,564 B2 8/2008 Flory
7,428,047 B2 9/2008 Oldham et al.
7,438,193 B2 10/2008 Yang et al.
7,444,053 B2 10/2008 Schmidt et al.
7,468,271 B2 12/2008 Golovchenko et al.
7,476,503 B2 1/2009 Turner et al.
7,553,730 B2 6/2009 Barth et al.
7,567,695 B2 7/2009 Frost et al.
7,595,023 B2 9/2009 Lewis et al.
7,609,309 B2 10/2009 Brown et al.
7,622,934 B2 11/2009 Hibbs et al.
7,625,706 B2 12/2009 Akeson et al.
7,651,599 B2 1/2010 Blaga et al.
7,666,593 B2 2/2010 Lapidus
7,670,770 B2 3/2010 Chou et al.
7,678,562 B2 3/2010 Ling
7,744,816 B2 6/2010 Su et al.
7,777,505 B2 8/2010 White et al.
7,803,607 B2 9/2010 Branton et al.
7,835,870 B2 11/2010 Nair et al.
7,838,873 B2 11/2010 Clevenger et al.
7,843,562 B2 11/2010 Chan et al.
7,846,738 B2 12/2010 Golovchenko et al.
7,849,581 B2 12/2010 White et al.
7,871,777 B2 1/2011 Schneider et al.
7,883,869 B2 2/2011 Ju et al.
7,897,338 B2 3/2011 Woo et al.
7,947,454 B2 5/2011 Akeson et al.
7,972,858 B2 7/2011 Meller et al.
8,105,846 B2 1/2012 Bayley et al.
8,206,568 B2 6/2012 Branton et al.
8,394,584 B2 3/2013 Timp et al.
8,394,640 B2 3/2013 Golovchenko et al.
8,440,403 B2 5/2013 Frayling
8,771,491 B2 * 7/2014 Huber ........................... 204/452
2002/0119455 A1 8/2002 Chan
2003/0003463 A1 1/2003 Rothberg et al.
2003/0064366 A1 4/2003 Hardin et al.
2003/0092005 A1 5/2003 Levene et al.
2003/0096220 A1 5/2003 Lafferty et al.
2003/0143614 A1 7/2003 Drmanac
2003/0148544 A1 8/2003 Nie et al.
2003/0207326 A1 11/2003 Su et al.
2003/0215881 A1 11/2003 Bayley et al.
2004/0033492 A1 2/2004 Chen
2004/0146430 A1 7/2004 Dugas
2004/0175710 A1 9/2004 Haushalter
2005/0014154 A1 1/2005 Weizenegger
2005/0019784 A1 1/2005 Su et al.
2005/0095599 A1 5/2005 Pittaro et al.
2005/0136408 A1 6/2005 Tom-Moy et al.
2005/0147992 A1 7/2005 Quake et al.
2005/0153284 A1 7/2005 Foldes-Papp et al.
2005/0164211 A1 7/2005 Hannah

(56) References Cited

U.S. PATENT DOCUMENTS

| | | | |
|---|---|---|---|
| 2005/0186576 | A1 | 8/2005 | Chan et al. |
| 2005/0186629 | A1 | 8/2005 | Barth |
| 2005/0227239 | A1 | 10/2005 | Joyce |
| 2005/0241933 | A1 | 11/2005 | Branton et al. |
| 2005/0282229 | A1 | 12/2005 | Su et al. |
| 2006/0003458 | A1 | 1/2006 | Golovchenko et al. |
| 2006/0019247 | A1 | 1/2006 | Su et al. |
| 2006/0019259 | A1 | 1/2006 | Joyce |
| 2006/0210995 | A1 | 9/2006 | Joyce |
| 2006/0231419 | A1 | 10/2006 | Barth et al. |
| 2006/0292041 | A1 | 12/2006 | Dugas et al. |
| 2007/0012865 | A1 | 1/2007 | Katzir et al. |
| 2007/0037199 | A1 | 2/2007 | Takahashi et al. |
| 2007/0054276 | A1 | 3/2007 | Sampson |
| 2007/0172858 | A1 | 7/2007 | Hardin et al. |
| 2007/0172865 | A1 | 7/2007 | Hardin et al. |
| 2007/0190542 | A1 | 8/2007 | Ling et al. |
| 2007/0190543 | A1 | 8/2007 | Livak |
| 2007/0202008 | A1 | 8/2007 | Schembri et al. |
| 2007/0215472 | A1 | 9/2007 | Slater et al. |
| 2007/0218494 | A1 | 9/2007 | Slater et al. |
| 2007/0224613 | A1 | 9/2007 | Strathmann |
| 2007/0231795 | A1 | 10/2007 | Su |
| 2007/0264623 | A1 | 11/2007 | Wang et al. |
| 2008/0032290 | A1 | 2/2008 | Young |
| 2008/0050752 | A1 | 2/2008 | Sun et al. |
| 2008/0187915 | A1 | 8/2008 | Polonsky et al. |
| 2008/0193956 | A1 | 8/2008 | Kricka et al. |
| 2008/0254995 | A1 | 10/2008 | Kim et al. |
| 2008/0261204 | A1 | 10/2008 | Lexow |
| 2008/0274905 | A1 | 11/2008 | Greene |
| 2008/0311375 | A1 | 12/2008 | Harnack et al. |
| 2009/0021735 | A1 | 1/2009 | Oldham et al. |
| 2009/0024331 | A1 | 1/2009 | Tomaney et al. |
| 2009/0029477 | A1 | 1/2009 | Meller et al. |
| 2009/0035777 | A1 | 2/2009 | Kokoris et al. |
| 2009/0061447 | A1 | 3/2009 | Schneider |
| 2009/0066315 | A1 | 3/2009 | Hu et al. |
| 2009/0136958 | A1 | 5/2009 | Gershow et al. |
| 2009/0137007 | A1 | 5/2009 | Korlach et al. |
| 2009/0185955 | A1 | 7/2009 | Nellissen |
| 2009/0222216 | A1 | 9/2009 | Hibbs et al. |
| 2009/0250615 | A1 | 10/2009 | Oldham et al. |
| 2009/0277869 | A1 | 11/2009 | Dugas |
| 2009/0298075 | A1 | 12/2009 | Travers et al. |
| 2009/0305278 | A1 | 12/2009 | Hardin et al. |
| 2010/0025249 | A1 | 2/2010 | Polonsky et al. |
| 2010/0029508 | A1 | 2/2010 | Austin et al. |
| 2010/0035260 | A1 | 2/2010 | Olasagasti et al. |
| 2010/0035268 | A1 | 2/2010 | Beechem et al. |
| 2010/0075309 | A1 | 3/2010 | Maxham et al. |
| 2010/0103416 | A1 | 4/2010 | Oldham et al. |
| 2010/0227913 | A1 | 9/2010 | Lyakhov et al. |
| 2010/0262379 | A1 | 10/2010 | Frazier |
| 2010/0292101 | A1 | 11/2010 | So |
| 2010/0331194 | A1 | 12/2010 | Turner et al. |
| 2011/0053284 | A1 | 3/2011 | Meller et al. |
| 2011/0172404 | A1 | 7/2011 | Luo et al. |
| 2011/0177498 | A1 | 7/2011 | Clarke et al. |
| 2011/0177978 | A1 | 7/2011 | Luo et al. |
| 2012/0055792 | A1 | 3/2012 | Gundlach et al. |
| 2012/0261261 | A1 | 10/2012 | Huber |
| 2013/0040827 | A1 | 2/2013 | Macevicz |
| 2013/0203050 | A1 | 8/2013 | Huber et al. |
| 2014/0087474 | A1 | 3/2014 | Huber |

FOREIGN PATENT DOCUMENTS

| | | |
|---|---|---|
| EP | 1682673 | 7/2006 |
| WO | WO 01/18247 | 3/2001 |
| WO | WO 2006/052882 | 5/2006 |
| WO | WO 2008/049795 | 5/2008 |
| WO | WO 2009/020682 | 8/2008 |
| WO | WO 2009/092035 | 1/2009 |
| WO | WO 2010/002883 | 2/2009 |
| WO | WO 2011/050147 | 7/2009 |
| WO | WO 2009/007743 | 1/2010 |
| WO | WO 2012/170499 | 1/2010 |
| WO | WO 2010/116595 | 10/2010 |
| WO | WO 2011/040996 | 4/2011 |
| WO | WO 2011/067559 | 4/2011 |
| WO | WO 2008/092760 | 6/2011 |
| WO | WO 2012/121756 | 9/2012 |
| WO | WO 2010/007537 | 12/2012 |

OTHER PUBLICATIONS

Algar, W. R. et al. "Quantum dots as donors in fluorescence resonance energy transfer for the bioanalysis of nucleic acids, proteins, and other biological molecules," *Anal Bioanal Chem*, vol. 391, abstract only, 2008.

Anderson, M. et al, "Next Generation DNA Sequencing and the Future of Genomic Medicine," *Genes*,vol. 1, pp. 38-69, 2010.

Baker, L.A. et al., "A makeover for membranes," *Nature Nanotechnology*, vol. 3, pp. 73-74, Feb. 2008.

Bayley, "Sequencing single molecules of DNA," *Current Opinion in Chemical Biology*,10(6), abstract only, Dec. 2006.

Begovich, A.B. et al., "A Missense Single-Nucleotide Polymorphism in a Gene Encoding a Protein Tyrosine Phosphatase (PTPN22) Is Associated with Rheumatoid Arthritis," *The American Journal of Human Genetics*, vol. 75, No. 2, pp. 330-337, Aug. 1, 2004.

Branton, D. et al, "The potential and challenges of nanopore sequencing," *Nature Biotechnology*, 26(10), pp. 1146-1153, Oct. 2008.

Butler, T. Z. et al., "Single-molecule DNA detection with an engineered MspA protein nanopore," *Proceedings of the National Academy of Sciences*, 105(52), pp. 20647-20652, Dec. 30, 2008.

Chan, E. Y. et al. "DNA Mapping Using Microfluidic Stretching and Single-Molecule Detection of Fluorescent Site-Specific Tags," *Genome Research*, vol. 14, pp. 1137-1146, 2004.

Chan, W.C. et al. "Quantum Dot Bioconjugates for Ultrasensitive Nonisotopic Detection," *Science*, vol. 281, pp. 2016-2018, Sep. 25, 1998.

Chansin, et al. "Single-Molecule Spactroscopy Using Nanoporous Membranes," *Nano Letters*,vol. 7, No. 9; pp. 2901-2906, 2007.

Chen, P. et al, "Atomic Layer Deposition to Fine-Tune the Surface Properties and Diameters of Fabricated Nanopores," *Nano Letters*, 4(7), pp. 1333-1337, 2004.

Cherf, G. et al, "Automated forward and reverse ratcheting of DNA in a nanopore at 5-A precision," *Nat Biotechnol.*, 30(4), 6 pages, Feb. 14, 2012.

Clarke, J. et al, "Continuous base identification for single-molecule nanopore DNA sequencing," *Nature Nanotechnology*, 4(4), pp. 265-270, Apr. 2009.

Danelon, C. et al. "Fabrication and Functionalization of Nanochannels by Electron-Beam-Induced Silicon Oxide Deposition," *Langmuir*, vol. 22, pp. 10711-10715, 2006.

Deamer,et al., "Characterization of Nucleic Acids by Nanopore Analysis," *Acc. Chem. Res.*, 35(10), pp. 817-825, 2002.

Deamer,et al., "Nanopores and nucleic acids: prospects for ultrarapid sequencing," *Trends in Biotechnology*,18(4), abstract only (2 pages), Apr. 1, 2000.

Deblois, R. et al, "Counting and Sizing of Submicron Particles by the Resistive Pulse Technique," *Rev. Sci. Instruments*, 41(7), pp. 909-916, Jul. 1970.

Dekker, C. C "Solid-state nanopores," *Nature Nanotechnology*, vol. 2, pp. 209-215, Apr. 2007.

Dela Torre, R. et al. "Fabrication and Characterization of Solid-state Nanopore Arrays for High Throughput DNA Sequencing," *Nanotechnology*,23(38), 12 pages, Sep. 28, 2012.

Dennis, A.M. et al., "Quantum Dot—Fluorescent Protein Pairs as Novel Fluorescence Resonance Energy Transfer Probes," *Nano Lett*, vol. 8, No. 5, pp. 1439-1445, 2008, American Chemical Society.

Etoh, et al. "An Image Sensor Which Captures 100 Consecutive Frames at 1000000 Frames/s," *IEEE Transactions on Electron Devices*,vol. 50. No. 1; pp. 144-151, Jan. 2003.

Fologea, et al. "Detecting Single Stranded DNA with a Solid State Nanopore," *Nano Letters*, 5 (10), abstract only, Aug. 31, 2005.

(56) References Cited

OTHER PUBLICATIONS

Freeman, J. et al, "Profiling the T-cell receptor beta-chain repertoire by massively parallel sequencing," Genome Research, vol. 19, pp. 1817-1824, Jun. 2009.
Gierlich, J. et al, "Synthesis of Highly Modified DNA by a Combination of PCR with Alkyne-Bearing Triphosphates and Click Chemistry," *Chem. Eur. J.*, vol. 13, pp. 9486-9494, 2007.
Grayson, A. et al, "A BioMEMS Review: MEMS Technology for Physiologically Integrated Devices," *Proceedings IEEE*, 92(1), pp. 6-21, Jan. 2004.
Gu, L. et al, "Single molecule sensing by nanopores and nanopore devices," *Analyst*,135(3), pp. 441-451, 2010.
Gupta, et al., "Single-molecule DNA sequencing technologies for future genomic research," *Trends in Biotechnology*, 26(11), pp. 602-611, Nov. 1, 2008.
Ha, T. et al., "Probing the interaction between two single molecules: fluorescence resonance energy transfer between a single donor and a single acceptor," *Proc. Natl. Acad. Sci USA*, vol. 93, No. 13, pp. 6264-6268, Jun. 25, 1996.
Hagan, B. "Sequencing single Molecules of DNA," *Current Opinion in Chemical Biology*, vol. 10, Isssue 6, pp. 628-637, 2006.
Hall, A. R. et al. "Hybrid pore formation by directed insertion of alpha hemolysin into solid-state nanopores," *Nature Nanotechnology*, 5(12), pp. 874-877, Dec. 2010.
He, H. et al., "Single Nonblinking CdTe Quantum Dots Synthesized in Aqueous Thiopropionic Acid," *Angew. Chem. Int. Ed.* vol. 45, pp. 7588-7591, Oct. 2006.
Heins, E.A. et al., "Detecting Single Porphyrin Molecules in a Conically Shaped Synthetic Nanopore," *Nano Letters*, 5(9), pp. 1824-1829, Jul. 26, 2005.
Heins, E.A. et al., "Detecting Single Porphyrin Molecules in a Conically Shaped Synthetic Nanopore," *Nano Letters*, 5(9), pp. 1824-1829, Jul. 26, 2005, Supporting Information.
Hemminger, "Visualizing and Understanding Complex MicrolNanonuidic Flow Behavior," Dissertation, The Ohio State University, 2010, available online at <http://etd.ohiolink.edulsend•pdf.cgUHemminger%200rin%20L.pdf?osu1275398565>.
Henriquez, R. et al, "The resurgence of Coulter counting for analyzing nanoscale objects," *The Analyst*, 129, pp. 478-482, 2004.
Hoevel, T. et al., "Cisplatin-Digoxigenin mRNA labeling for nonradioactive detection of mRNA hybridized onto nucleic acid cDNA arrays," *Biotechniques*, vol. 27, No. 5, pp. 1064-1067, Nov. 1999.
Holt, R. et al, "The new paradigm of flow cell sequencing," *Genome Research*, vol. 18, pp. 839-846, 2008.
Iqbal, S. M. et al., "Solid-state nanopore channels with DNA selectivity," *Nature Nanotechnology*, pp. 1-6, Apr. 1, 2007.
Ito, T. et al., "Observation of DNA transport through a single carbon nanotube channel using fluorescence microscopy," *Chem. Commun*, vol. 12, pp. 1482-1483, 2003.
Jagtiani, A. et al, "A label-free high throughput resistive-pulse sensor for simultaneous differentiation and measurement of multiple particle-laden analytes," *J. Micromech. Microeng.*, 16, pp. 1530-1539, 2006.
Kang, X. et al., "A storable encapsulated bilayer chip containing a single protein nanopore," *J Am Chem Soc*. vol. 129, No. 15, pp. 4701-4705, Mar. 22, 2007.
Kasianowicz, J.J. et al., "Characterization of Individual Polynucleotide Molecules Using a Membrane Channel," *Proc. Natl. Acad. Sci USA*, vol. 93, pp. 13770-13773, Nov. 1996.
Keyser, U. F. "Controlling molecular transport through nanopores," *Journal of the Royal Society Interface*,10 page, published online 2011.
Kircher, M. et al, "High-throughput DNA sequencing-concepts and limitations," *Bioessays*, vol. 32, pp. 524-536, 2010.
Kleefen, A. et al. "Multiplexed Parallel Single Transport Recordings on Nanopore Arrays," *Nano Letters*, vol. 10, pp. 5080-5087, 2010.
Kocer, A. et al. "Nanopore sensors: From hybrid to abiotic systems," *Biosensors and Bioelectronics*, vol. 38, 10 pp., 2012.
Kolb, H. et al, "Click Chemistry: Diverse Chemical Function from a Few Good Reactions," *Angew. Chem. Int. Ed.*, vol. 40, pp. 2005-2021, 2001.
Kristensen, V. N. et al., "High-Throughput Methods for Detection of Genetic Variation," *BioTechniques*, 30(2), pp. 318-332, Feb. 2001.
Lerner, H. et al, "Prospects for the Use of Next-Generation Sequencing Methods in Ornithology," *The Auk*, 127(1), pp. 4-15, 2010.
Li et al., "DNA Molecules and Configurations in a Solid-State Nanopore Microscope," *Nat. Mater*, vol. 2, pp. 611-615, Sep. 2003.
Li, J. et al., "Nanoscale Ion Beam Sculpting," *Nature*, vol. 412, 11 pages, Jul. 12, 2001.
Lin, B. et al., "Recent Patents and Advances in the Next-Generation Sequencing Technologies," *Recent Patents on Biomedical Engineering*, vol. 1, No. 1, pp. 60-67, 2008, Benthan Science Publishers Ltd.
Lo, C.J. et al., "Fabrication of symmetric sub-5 nm nanopores using focused ion and electron beams," *Nanotechnology*, vol. 17, No. 13, pp. 3264-3267, Jul. 2006.
Maitra, R. D. et al. "Recent advances in nanopore sequencing," *Electrophoresis*, vol. 33, pp. 3418-3428, 2012.
Manrao, E. et al. "Reading DNA at single-nucleotide resolution with a mutant MspA nanopore and phi29 DNA polymerase," *Nat Biotechnol*, 30(4), 6 pages, Mar. 25, 2012.
McNally, et al. "Optical recognition of converted DNA nucleotides for single-molecule DNA sequencing using nanopore arrays," *Nano Letters*, vol. 10, No. 6; pp. 2237-2244, Jun. 9, 2010.
Meagher, R. J. et al. "Free-solution electrophoresis of DNA modified with drag-tags at both ends," *Electrophoresis*,vol. 27, pp. 1702-1712, 2006.
Meagher, R. J. et al. "Sequencing of Dna by Free-Solution Capillary Electrophoresis Using a Genetically Engineered Protein Polymer Drag-Tag," *Anal. Chem.*, vol. 80, pp. 2842-2848, Apr. 15, 2008.
Medintz, I.L. et al. "A fluorescence resonance energy transfer-derived structure of a quantum dot-protein bioconjugate nonassembly," *PNAS*, 101(26), pp. 9612-9617, Jun. 29, 2004.
Meller, A. et al., "Rapid nanopore discrimination between single polynucleotide molecules," *The National Academy of Sciences*, 2000, 7 pages.
Meller, A. et al., "Voltage-Driven DNA Translocations through a Nanopore," *Phys. Rev. Lett*. 86(15), pp. 3435-3438, Apr. 2001.
Meller, et al., "Single Molecule Measurements of DNA Transport through a Nanopore," *Electrophoresis*,vol. 23, pp. 2583-2591, 2002.
Metzker, M. "Sequencing technologies—the next generation," *Nature Review Genetics*, vol. 11, pp. 31-46, Jan. 2010.
Mir, K., "Ultrasensitive RNA profiling: Counting single molecules on microarrays," *Genome Research*,16:1195-1197, Oct. 2006.
Nakane, J. et al, "Evaluation of nanopores as candidates for electronic analyte dectection," *Electrophoresis*, vol. 23, pp. 2592-2601, 2002.
Nakane, J. et al, "Nanopore sensors for nucleic acid analysis," *J. Phys. Condens. Matter*, Matter 15, pp. R1365-R1393, 2003.
Ogura, Y. et al., "A Frameshift Mutation in NOD2 Associated with Susceptibility to Crohn's Disease," *Nature*, vol. 411, pp. 603-606, May 31, 2001, Macmillan Magazine Ltd.
Rasnik, I. et al., "Nonblinking and long-lasting single-molecule fluorescence imaging," *Nature Methods*, 3(11), pp. 891-893, Nov. 2006.
Reed, M.A. "Quantum Dots," *Scientific American*, pp. 118-123, Jan. 1993.
Resch-Genger, U. et al. "Quantum dots versus organic dyes as fluorescent labels," *Nature Methods*,5(9), pp. 763-775, Sep. 2008.
Rhee, M. et al., "Nanopore Sequencing Technology: Nanopore Preparations," *Trends in Biotechnology*, vol. 25, No. 4, pp. 174-181, Apr. 2007.
Rhee, M. et al., "Nanopore Sequencing Technology: research trends and applications," *Trends in Biotechnology*, vol. 24, No. 12, pp. 580-586, Dec. 2008.
Sabanayagam, C.R. et al., "Long time scale blinking kinetics of cyanine fluorophores conjugated to DNA and its effect on Forster resonance energy transfer," *J. Chem. Phys.*, 123(22), pp. 224708-1 to 224708-7, Dec. 2005.
Sanger, F. et al., "DNA Sequencing with Chain-Terminating Inhibitors," *Proc. Natl. Acad. Sci. USA*, vol. 74, No. 12, pp. 5463-5467, Dec. 1977.

(56) References Cited

OTHER PUBLICATIONS

Schumacher, S. et al, "Highly-integrated lab-on-chip system for point-of-care multiparameter analysis," *Lab on a Chip*, 12(3), pp. 464-473, 2012.
Shaffer, C., "Next generation sequencing outpaces expectations," *Nature Biotechnology*, vol. 25, p. 149, Feb. 2007.
Shi, L. et al. "Luminescent Quantum Dots Fluorescence Resonance Energy Transfer-Based Probes for Enzymatic Activity and Enzyme Inhibitors," *Anal. Chem*, 79(1), pp. 208-214, Jan. 1, 2007.
Song, L. et al., "Structure of Staphylococcal alpha-hemolysin, a heptameric transmembrane protein," *Science*, vol. 274, No. 5294, pp. 1859-1866, Dec. 13, 1996.
Soni, et al. "Progress toward Ultrafast DNA Sequencing Using Solid-State Nanopores," *Clinical Chemistry*, vol. 53, No. 11; pp. 1996-2001, 2007.
Soni, G. V. et al. "Synchronous optical and electrical detection of biomolecules traversing through solid-state nanopores," *Review of Scientific Instruments*, pp. 014301-1-014301-7, published online Jan. 19, 2010.
Storm, A. J. et al. "Fabrication of solid-state nanopores with single-nanometre precision," *Nature Materials*, vol. 2, pp. 537-540, Aug. 2003.
Strittmatter, W.J. et al, "Apolipoprotein E and Alzheimer's Disease," *Annual Review of Neuroscience*, vol. 19, pp. 53-77, 1996.
Stryer, L., "Fluorescence Energy Transfer as a Spectroscopic Ruler," *Annual Review of Biochemistry*, vol. 47, pp. 819-846, Jul. 1978.
Telenius, H. et al., "Degenerate oligonucleotide-primed PCR: General amplification of target DNA by a single degenerate primer," *Genomics*, vol. 13, No. 3, pp. 718-725, Jul. 1992.
Thompson, J. F. et al. "The properties and applications of single-molecule DNA sequencing," *Genome Biology*, 12(217), 10 pp., 2011.
Tucker, T. et al, "Massively Parallel Sequencing: The Next Big Thing in Genetice Medicine," *Am. J. Human Genet.*, vol. 85, pp. 142-154, Aug. 2009.
Turner, E. et al, "Methods for Genomic Partitioning," *Annual Review of Genomics and Human Genetics*, vol. 10, pp. 263-284, 2009.
Venkatesen, B. M. et al. "Lipid bilayer coated A1203 naopore sensors: towards a hybrid biological solid-state nanopore," *Biomed Microdevices*, 13(4), 21 pages, 2011.
Venkatesen, B. M. et al. "Nanopore sensors for nucleic acid analysis," *Nature Nanotechnology*,vol. 6, pp. 615-624, Oct. 2011.
Vercoutere, W. et al., "Rapid discrimination among individual DNA hairpin molecules at single-nucleotide resolution using an ion channel," *Nature Biotechnology*, vol. 19, pp. 248-252, Mar. 2001.
Voelkerding, K. et al, "Next-Generation Sequencing: From Basic Research to Diagnostic," Clinical Chemistry, 55:4, pp. 641-658, 2009.
Walker, B. et al. "Key Residues for Membrane Binding, Oligomerization, and Pore Forming Activity of Staphylococcal alpha-Hemolysin Identified by Cysteine Scanning Mutagenesis and Targeted Chemical Modification," *Journal of Biological Chemistry*, 270(39), pp. 23065-23071, Sep. 29, 1995.
Wang, H. et al., "Nanopores with a spark for single-molecule detection," Nature Biotechnology, vol. 19, pp. 622-633, Jul. 2001.
Wanunu, M. et al. "Chemically Modified Solid-State Nanopores," *Nano Letters*, 7(6), pp. 1580-1585, 2007.
Wanunu, M. et al."Nanopores: A journey towards DNA sequencing," *Physics of Life Reviews*, vol. 9, pp. 125-158, 2012.
Won, J. et al. "Protein polymer drag-tags for DNA separations by end-labeled free electrophoresis," *Electrophoresis*, vol. 26, pp. 2138-2148, 2005.
Wu, X. et al, "Microfluidic differential resistive pulse sensors," *Electrophoresis*, 29(13), pp. 2754-2759, 2008.
Xu, et al., "Perspectives and Challenges of Emerging Single-Molecule DNA Sequencing Technologies," *SMALL*, 5(53), pp. 2638-2649, Dec. 4, 2009.
Yan, X. et al, "Parallel Fabrication of Sub-50-nm Uniformly Sized Nanaparticles by Deposition through a Patterned Silicon Nitride Nanostencil," *Nano Letters*, 5(6), pp. 1129-1134, 2005.
Yang, J. et al. "Rapid and precise scanning helium ion microscope milling of solid-state nanopores for biomolecule detection," *Nanotechnology*, vol. 22, 6 pages, 2011.
Zhang, L. et al., "Whole genome amplification from a single cell: implications for genetic analysis," *Proc. Natl. Acad. Sci. USA*, vol. 89, No. 13, pp. 5847-5851, Jul. 1, 1992.
Zhe, J. et al, "A micromachined high throughput Coulter counter for bioparticle detection and counting," *J. Micromech. Microeng.*, vol. 17, pp. 304-313, 2007.
Zheng, S. et al. "Parallel analysis of biomolecules on a microfabricated capillary array chip," *Electrophoresis*, vol. 26, abstract only, Mar. 2006.
Zwolak, M. et al., "Colloquium: Physical approaches to DNA sequencing and detection," *Reviews of Modern Physics*, 80(1), pp. 141-165, Jan. 2, 2008.
Tamura, T., *Molecular Biology illustrated*, revised Second Edition, pp. 174-175, Jan. 1, 2003.
US 8,008,014, 08/2011, Gershow et al. (withdrawn)

* cited by examiner

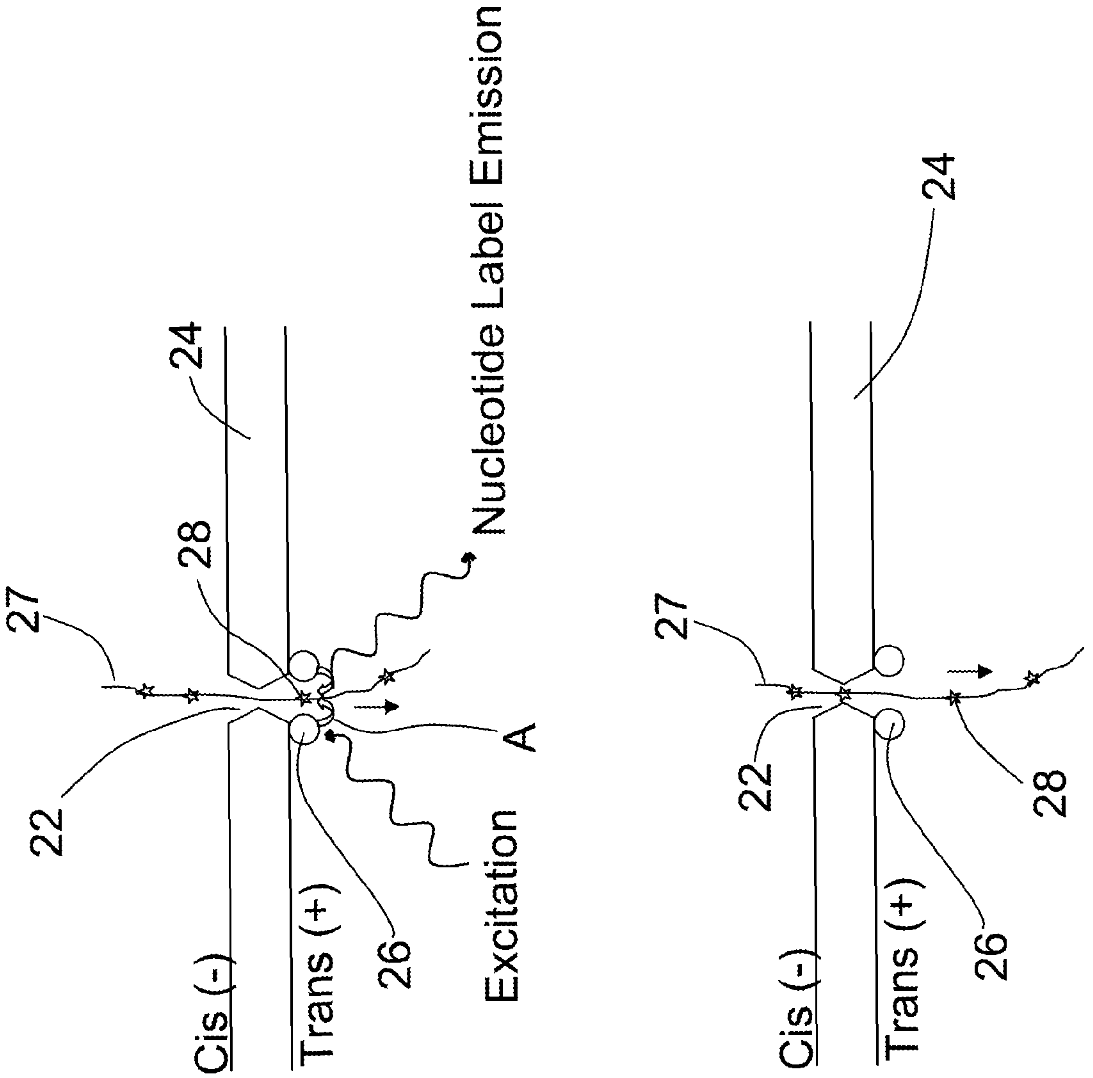
Figure 2A FRET
Figure 2B No FRET

FRET

No FRET

FRET

Quenching

No Quenching

Quenching

No Quenching

```
                         SEQUENCE LISTING


<160> NUMBER OF SEQ ID NOS: 1

<210> SEQ ID NO 1
<211> LENGTH: 17
<212> TYPE: DNA
<213> ORGANISM: Artificial Sequence
<220> FEATURE:
<223> OTHER INFORMATION: Sample nucleic acid sequence

<400> SEQUENCE: 1

gaagtttagt tacagcc                                                   17
```

ULTRAFAST SEQUENCING OF BIOLOGICAL POLYMERS USING A LABELED NANOPORE

CROSS-REFERENCE TO RELATED APPLICATION

This application is a continuation of U.S. patent application Ser. No. 13/426,515 filed Mar. 21, 2012, which is a continuation of International Patent Application No. PCT/US2010/034809 filed May 13, 2010, which claims the benefit of priority to U.S. Prov. Pat. App. 61/277,939 filed Sep. 30, 2009, the contents of which are incorporated herein by reference in their entirety.

REFERENCE TO A "SEQUENCE LISTING"

This application contains a sequence listing submission in computer readable form (.txt) which is incorporated herein by reference in its entirety.

BACKGROUND

DNA is a long bio-polymer made from repeating units called nucleotides. DNA polymers can be enormous molecules containing millions of nucleotides e.g. the human genome contains a total of 3 billion nucleotides. In living organisms, DNA does not usually exist as a single molecule, but instead as a tightly-associated pair of molecules. These two long strands intertwine like vines, in the shape of a double helix. The nucleotide repeats contain both a phosphate backbone which holds the chain together, and a base, which interacts with the other DNA strand in the helix. This interaction between the bases of the two DNA strands is called hydrogen bonds and they hold the double helix together. There are four different types of bases: Adenine (A), Cytosine (C), Guanine (G) and Thymine (T). Each type of base in one strand forms a hydrogen bond with just one type of base in the complementary strand, with A bonding only to T, and C bonding only to G.

The sequence of the four bases determines the genetic information contained in DNA. Revealing the sequence of the four building blocks of polynucleic acid is called sequencing. Polynucleic acid comprises bases of nucleosides chemically bound in a linear fashion. "DNA" (De-oxyribonucleic acid) and "RNA" (Ribonucleic acid) are examples of such polynucleic acid molecules. The particular order or "sequence" of these bases in a given gene determines the structure of the protein encoded by the gene. Furthermore, the sequence of bases surrounding the gene typically contains information about how often the particular protein should be made, in which cell types etc.

The complete nucleotide sequence of all DNA polymers in a particular individual is known as that individual's "genome". In 2003 the human genome project was finished and a draft version of the human DNA sequence was presented. It took 13 years, 3 billion US $ and the joint power of multiple sequencing centers to achieve this scientific milestone which was compared in significance to the arrival of men on the moon. The method used for this giant project is called Sanger sequencing (Sanger, F. et al., Proc. Natl. Acad. Sci. USA (1977) 74, 5463-5467 and Smith et al., U.S. Pat. No. 5,821,058). Although major technical improvements were made during this time, the classical sequencing method has some key-disadvantages:

- Laborious sample preparation, including subcloning of DNA fragments in bacteria
- Expensive automation

- Cost prohibitive molecular biology reagents
- Limited throughput which results in years to finish sequencing whole genomes Multiple diseases have a strong genetic component (Strittmatter, W. J. et al., Annual Review of Neuroscience 19 (1996): 53-77; Ogura, Y. et al., Nature 411, (2001): 603-606; Begovich, A. B. et al., American Journal of Human Genetics 75, (2004): 330-337). With the completion of the Human Genome Project and an ever deepening comprehension of the molecular basis of disease, medicine in the 21st century is poised for a revolution called "molecular diagnostics". Most commercial and academic approaches in molecular diagnostics assess single nucleotide variations (SNPs) or mutations to identify DNA aberrations. These technologies, although powerful, will analyze only a small portion of the entire genome. The inability to accurately and rapidly sequence large quantities of DNA remains an important bottleneck for research and drug development (Shaffer, C., Nat Biotech 25 (2007): 149). Clearly, there is a need for the development of improved sequencing technologies that are faster, easier to use, and less expensive.

BRIEF SUMMARY

Variations described herein relate to methods, systems and/or devices for detecting the sequence composition of biological polymers. For example, methods and devices are described herein which are capable of ultrafast polymer sequencing utilizing a labeled pore or nanopore and a biological polymer with labeled monomer building blocks.

Methods and systems for sequencing a biological molecule or polymer, e.g., a nucleic acid, are provided. One or more donor labels, which are positioned on, attached or connected to a pore or nanopore, may be illuminated or otherwise excited. A polymer labeled with one or more acceptor labels, may be translocated through the nanopore. For example, a polymer having one or more monomers labeled with one or more acceptor labels, may be translocated through the nanopore. Either before, after or while the labeled monomer of the polymer or molecule passes through, exits or enters the nanopore and when an acceptor label comes into proximity with a donor label, energy may be transferred from the excited donor label to the acceptor label of the monomer or polymer. As a result of the energy transfer, the acceptor label emits energy, and the emitted energy is detected or measured in order to identify the monomer, e.g., the nucleotides of a translocated nucleic acid molecule, which is associated with the detected acceptor label energy emission. The nucleic acid or other polymer may be deduced or sequenced based on the detected or measured energy emission from the acceptor labels and the identification of the monomers or monomer sub units.

BRIEF DESCRIPTION OF THE SEVERAL VIEWS OF THE DRAWINGS

FIG. 2A illustrates one variation of a FRET (Förster Resonance Energy Transfer) interaction between a pore label on a synthetic nanopore and a nucleic acid label on a nucleic acid which is being translocated through the synthetic nanopore.

FIG. 2B illustrates translocation of the labeled nucleic acid through a synthetic nanopore at a point in time where no FRET is taking place.

DETAILED DESCRIPTION

Figures 1A, 1B:
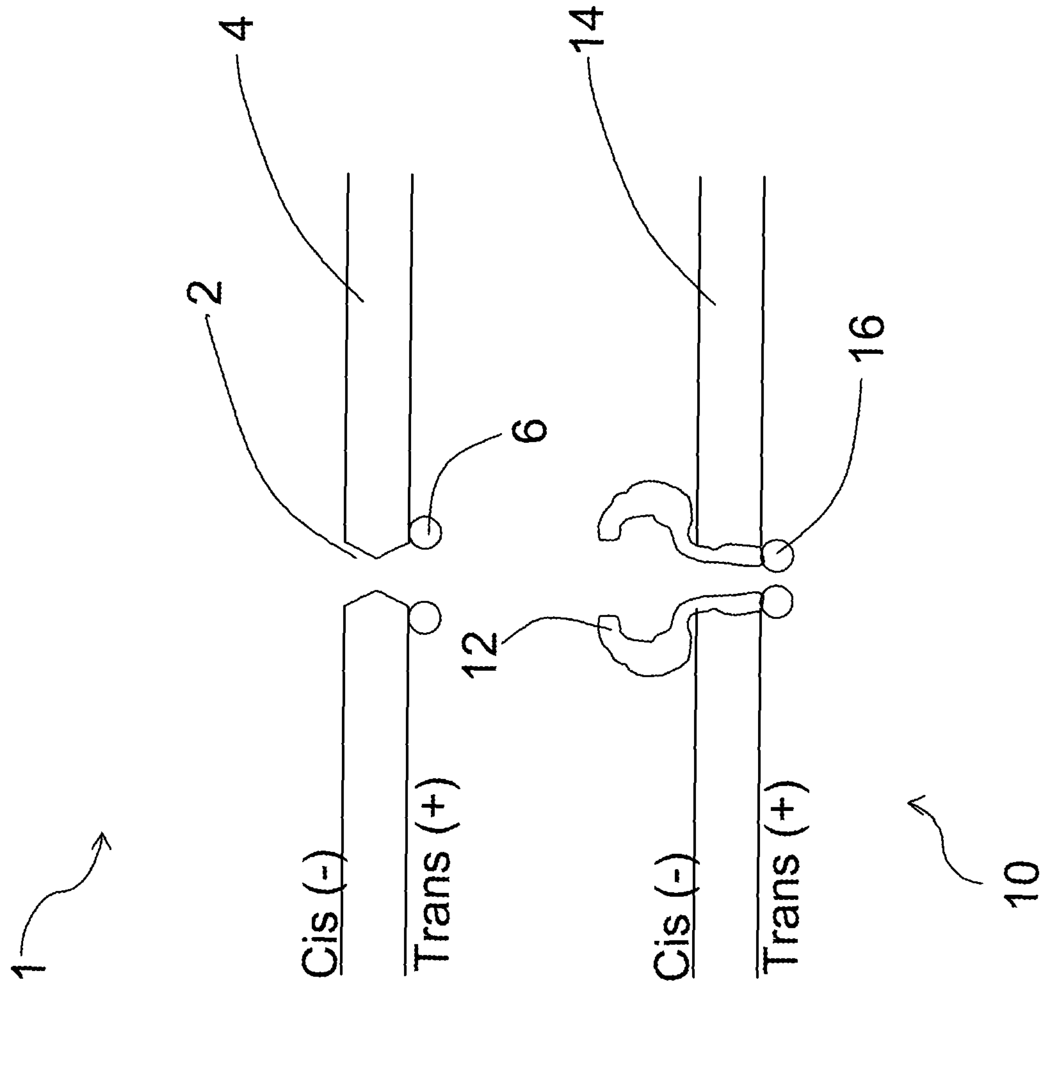
FIG. 1A illustrates a variation of a synthetic nanopore having a pore label attached thereto.
FIG. 1B illustrates a variation of a protein nanopore having a pore label attached thereto.

A method and/or system for sequencing a biological polymer or molecule (e.g., a nucleic acid) may include exciting one or more donor labels attached to a pore or nanopore. A biological polymer may be translocated through the pore or nanopore, where a monomer of the biological polymer is labeled with one or more acceptor labels. Energy may be transferred from the excited donor label to the acceptor label of the monomer as, after or before the labeled monomer passes through, exits or enters the pore or nanopore. Energy emitted by the acceptor label as a result of the energy transfer may be detected, where the energy emitted by the acceptor label may correspond to or be associated with a single or particular monomer (e.g., a nucleotide) of a biological polymer. The sequence of the biological polymer may then be deduced or sequenced based on the detection of the emitted energy from the monomer acceptor label which allows for the identification of the labeled monomer. A pore, nanopore, channel or passage, e.g., an ion permeable pore, nanopore, channel or passage may be utilized in the systems and methods described herein.

Nanopore energy transfer sequencing (NETS) can be used to sequence nucleic acid. NETS can enable the sequencing of whole genomes within days for a fraction of today's cost which will revolutionize the understanding, diagnosis, monitoring and treatment of disease. The system or method can utilize a pore or nanopore (synthetic or protein-based) of which one side, either the cis (−) or trans (+) side of the pore is labeled with one or multiple or a combination of different energy absorbers or donor labels, such as fluorophores, fluorescent proteins, quantum dots, metal nanoparticles, nanodiamonds, etc. Multiple labels and methods of labeling a nanopore are described in U.S. Pat. No. 6,528,258, the entirety of which is incorporated herein by reference.

A nucleic acid can be threaded through a nanopore by applying an electric field through the nanopore (Kasianowicz, J. J. et al., Characterization of individual polynucleotide molecules using a membrane channel. *Proc. Natl. Acad. Sci USA* 93 (1996): 13770-13773). A nucleic acid to be translocated through the nanopore may undergoe a labeling reaction where naturally occurring nucleotides are exchanged with a labeled, energy emitting or absorbing counterpart or modified counterparts that can be subsequently modified with an energy emitting or absorbing label, i.e., an acceptor label. The labeled nucleic acid may then be translocated through the nanopore and upon entering, exiting or while passing through the nanopore a labeled nucleotide comes in close proximity to the nanopore or donor label. For example, within 1-10 nm or 1-2 nm of the nanopore donor label. The donor labels may be continuously illuminated with radiation of appropriate wavelength to excite the donor labels. Via a dipole-dipole energy exchange mechanism called FRET (Stryer, L. *Annu Rev Biochein.* 47 (1978): 819-846), the excited donor labels transfer energy to a bypassing nucleic acid or acceptor label. The excited acceptor label may then emit radiation, e.g., at a lower energy than the radiation that was used to excite the donor label. This energy transfer mechanism allows the excitation radiation to be "focused" to interact with the acceptor labels with sufficient resolution to generate a signal at the single nucleotide scale.

A nanopore may include any opening positioned in a substrate that allows the passage of a molecule through the substrate. For example, the nanopore may allow passage of a molecule that would otherwise not be able to pass through that substrate. Examples of nanopores include proteinaceous or protein based pores or synthetic pores. A nanopore may have an inner diameter of 1-10 nm or 1-5 nm or 1-3 nm.

Examples of protein pores include but are not limited to, alpha-hemolysin, voltage-dependent mitochondrial porin (VDAC), OmpF, OmpC, MspA and LamB (maltoporin) (Rhee, M. et al., *Trends in Biotechnology,* 25(4) (2007): 174-181). Any protein pore that allows the translocation of single nucleic acid molecules may be employed. A pore protein may be labeled at a specific site on the exterior of the pore, or at a specific site on the exterior of one or more monomer units making up the pore forming protein.

A synthetic pore may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane.

Synthetic nanopores may be created using a variety of methods. For example, synthetic nanopores may be created by ion beam sculpting (Li, J. et al., *Nature* 412 (2001): 166-169) where massive ions with energies of several thousand electron volts (eV) cause an erosion process when fired at a surface which eventually will lead to the formation of a nanopore. A synthetic nanopore may be created via latent track etching. For example, a single conical synthetic nanopore may be created in a polymer substrate by chemically etching the latent track of a single, energetic heavy ion. Each ion produces an etchable track in a polymer foil, forming a one-pore membrane (Heins, E. A. et al., *Nano Letters* 5 (2005): 1824-1829). A synthetic nanopore may also be created by a method called Electron beam-induced fine tuning. Nanopores in various materials have been fabricated by advanced nanofabrication techniques, such as FIB drilling and electron (E) beam lithography, followed by E-beam assisted fine tuning techniques. With the appropriate electron beam intensity applied, a previously prepared nanopore will start to shrink. The change in pore diameter may be monitored in real-time using a TEM (transmission electron microscope), providing a feedback mechanism to switch off the electron beam at any desired dimension of the nanopore (Lo, C. J. et al., *Nanotechnology* 17 (2006): 3264-67).

A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., *Chem. Commun.* 12 (2003): 1482-83).

A pore may have two sides. One side is referred to as the "cis" side and faces the (−) negative electrode or a negatively charged buffer/ion compartment or solution. The other side is referred to as the "trans" side and faces the (+) electrode or a positively charged buffer/ion compartment or solution. A biological polymer, such as a labeled nucleic acid molecule or polymer can be pulled or driven through the pore by an electric field applied through the nanopore, e.g., entering on the cis side of the nanopore and exiting on the trans side of the nanopore.

A nanopore or pore may be labeled with one or more donor labels. For example, the cis side or surface and/or trans side or surface of the nanopore may be labeled with one or more donor labels. The label may be attached to the base of a pore or nanopore or to another portion or monomer making up the nanopore or pore A label may be attached to a portion of the membrane or substrate through which a nanopore spans or to a linker or other molecule attached to the membrane, substrate or nanopore. The nanopore or pore label may be positioned or attached on the nanopore, substrate or membrane such that the pore label can come into proximity with an acceptor label of a biological polymer, e.g., a nucleic acid, which is translocated through the pore. The donor labels may have the same or different emission or absorption spectra.

The labeling of a pore structure may be achieved via covalent or non-covalent interactions. Examples of such interactions include but are not limited to interactions based on hydrogen bonds, hydrophobic interactions, electrostatic interactions, ionic interactions, magnetic interactions, Van der Walls forces or combinations thereof.

A donor label may be placed as close as possible to the aperture of a nanopore without causing an occlusion that impairs translocation of a nucleic acid through the nanopore (see e.g., FIG. 1). A pore label may have a variety of suitable properties and/or characteristics. For example, a pore label may have energy absorption properties meeting particular requirements. A pore label may have a large radiation energy absorption cross-section, ranging, for example, from about 0 to 1000 nm or from about 200 to 500 nm. A pore label may absorb radiation within a specific energy range that is higher than the energy absorption of the nucleic acid label. The absorption energy of the pore label may be tuned with respect to the absorption energy of a nucleic acid label in order to control the distance at which energy transfer may occur between the two labels. A pore label may be stable and functional for at least 10^6 or 10^9 excitation and energy transfer cycles.

FIG. 1A shows a variation of a pore/substrate assembly 1. The pore/substrate assembly 1 includes a synthetic pore or nanopore 2 which has a pore label 6 attached thereto. The assembly may also include a substrate 4, e.g., a solid substrate, and the synthetic nanopore 2 is positioned in the substrate 4. The synthetic nanopore 2 is modified at the trans (+) side with one or more pore labels 6. The pore label 6 is attached to the base of the synthetic nanopore 2 in a manner such that the label 6 does not lead to inclusion or impair the translocation of a nucleic acid through the synthetic nanopore 2.

FIG. 1B shows a variation of a pore/lipid bilayer assembly 10. The pore/lipid bilayer assembly 10 includes a protein nanopore 12 which has a pore label 16 attached thereto. The assembly may also include a lipid bilayer 14 and the protein nanopore 12 is positioned in the lipid bilayer 14. The protein nanopore 12 is modified at the trans (+) side with one or more pore labels 16. The pore label 16 is attached to the base of the protein nanopore 12 in a manner such that the label 16 does not lead to inclusion or impair the translocation of a nucleic acid through the protein nanopore 12.

A protein nanopore can be embedded in a phospholipid bilayer or derivatizations thereof. Phospholipids are comprised of, but not limited to diphytanoyl-phospatidylcoline, soybean azolectin, 1,2-Diphytanoyl-sn-glycero-3-phosphocholine. A lipid bilayer can also be prepared by a mixture of different phospholipids. Possible solvents for phospholipids are hexadecane, pentane, chloroform or any other suitable organic solvent. A lipid bilayer may be prepared in variety of ways known to those having ordinary skill in the art.

A lipid bilayer (e.g., including the above mentioned phospholipids) having a pore protein may be prepared according to the following method: A 10-25 μm thick Teflonfilm (Septum) with a 1-100 μm aperture separates two buffer compartments made out of Teflon. The septum/aperture is primed with 10% hexadecane in pentane on each side and after evaporation of the solvent the buffer compartments are filled with 1 molar KCl. 1,2-Diphytanoyl-sn-glycero-3-phosphocholine (Avanti, 10 mg/mL in pentane) is added to each buffer compartment and the pentane is allowed to evaporate leaving behind lipid monolayers. Lowering and raising the liquid level in the chamber below and above the aperture caused lipid bilayers to be formed as needed. The formation of the bilayer is measured by applying voltage via Ag/AgCl electrodes.

Once the bilayer has formed the ionic current is completely eliminated. With the bilayer in place a dilute solution of pore protein is added to the cis-chamber. Pore proteins are chosen from a group of proteins such as, but not limited to, alpha-hemolysin, voltage-dependent mitochondrial porin (VDAC), Anthrax porin, OmpF, OmpC and LamB (maltoporin). The pore will self assemble and integrate into the lipid bilayer. Integration of the pore protein can be measured by a small but constant current. Typically, one inserted hemolysin pore can carry an ionic current of approximately 120 pA (picoAmperes), with an applied voltage of +120 mV (millivolts). The membrane can be protected by a second layer of a polymeric structure, comprising but not limited to Agarose, Polyacrylamide, etc. (Kang, X.-F. et al., *J Am Chem. Soc.* 129 (2007): 4701-4705).

Various polymers or molecules may be attached to a lipid bilayer having a pore protein therein to provide additional stability and support to the pore/membrane assembly and the pore should the membrane be damaged.

A pore label may include one or more Quantum dots. A Quantum dot has been demonstrated to have many or all of the above described properties and characteristics found in suitable pore labels (Bawendi M. G. in U.S. Pat. No. 6,251,303). Quantum Dots are nanometer scale semiconductor crystals that exhibit strong quantum confinement due to the crystals radius being smaller than the Bohr exciton radius. Due to the effects of quantum confinement, the bandgap of the quantum dots increases with decreasing crystal size thus allowing the optical properties to be tuned by controlling the crystal size (Bawendi M. G. et al., in U.S. Pat. No. 7,235,361 and Bawendi M. G. et al., in U.S. Pat. No. 6,855,551).

One example of a Quantum dot which may be utilized as a pore label is a CdTe quantum dot which can be synthesized aqueously. A CdTe quantum dot may be functionalized with a nucleophilic group such as primary amines, thiols or functional groups such as carboxylic acids. A CdTe quantum dot may include a mercaptopropionic acid capping ligand, which has a carboxylic acid functional group that may be utilized to covalently link a quantum dot to a primary amine on the exterior of a protein pore. The cross-linking reaction may be accomplished using standard cross-linking reagents (homo-bifunctional as well as hetero-bifunctional) which are known to those having ordinary skill in the art of bioconjugation. Care may be taken to ensure that the modifications do not impair or substantially impair the translocation of a nucleic acid through the nanopore. This may be achieved by varying the length of the employed crosslinker molecule used to attach the donor label to the nanopore.

The primary amine of the Lysin residue 131 of the natural alpha hemolysin protein (Song, L. et al., *Science* 274, (1996): 1859-1866) may be used to covalently bind carboxy modified CdTe Quantum dots via 1-Ethyl-3-[3-dimethylaminopropyl] carbodiimide hydrochloride/N-hydroxysulfosuccinimide (EDC/NHS) coupling chemistry.

A variety of methods, mechanisms and/or routes for attaching one or more pore labels to a pore protein may be utilized. A pore protein may be genetically engineered in a manner that introduces amino acids with known properties or various functional groups to the natural protein sequence. Such a modification of a naturally occurring protein sequence may be advantageous for the bioconjugation of Quantum dots to the pore protein. For example, the introduction of a Cystein residue would introduce a thiol group that would allow for the direct binding of a Quantum dot, such as a CdTe quantum dot, to a pore protein. Also, the introduction of a Lysin residue would introduce a primary amine for binding a Quantum dot. The introduction of glutamic acid or aspartic acid would introduce a carboxylic acid moiety for binding a Quantum dot. These groups are amenable for bioconjugation with a Quantum dot using either homo- or hetero-bifunctional crosslinker molecules. Such modifications to pore proteins aimed at the introduction of functional groups for bioconjugation are known to those having ordinary skill in the art. Care should be taken to ensure that the modifications do not impair or substantially impair the translocation of a nucleic acid through the nanopore.

The nanopore label can be attached to a protein nanopore before or after insertion of said nanopore into a lipid bilayer. Where a label is attached before insertion into a lipid bilayer, care may be taken to label the base of the nanopore and avoid random labeling of the pore protein. This can be achieved by genetic engineering of the pore protein to allow site specific attachment of the pore label (see section 0047). An advantage of this approach is the bulk production of labeled nanopores. Alternatively, a labeling reaction of a pre-inserted nanopore may ensure site-specific attachment of the label to the base (trans-side) of the nanopore without genetically engineering the pore protein.

A biological polymer, e.g., a nucleic acid molecule or polymer, may be labeled with one or more acceptor labels. For a nucleic acid molecule, each of the four nucleotides or building blocks of a nucleic acid molecule may be labeled with an acceptor label thereby creating a labeled (e.g., fluorescent) counterpart to each naturally occurring nucleotide. The acceptor label may be in the form of an energy accepting molecule which can be attached to one or more nucleotides on a portion or on the entire strand of a converted nucleic acid.

A variety of methods may be utilized to label the monomers or nucleotides of a nucleic acid molecule or polymer. A labeled nucleotide may be incorporated into a nucleic acid during synthesis of a new nucleic acid using the original sample as a template ("labeling by synthesis"). For example, the labeling of nucleic acid may be achieved via PCR, whole genome amplification, rolling circle amplification, primer extension or the like or via various combinations and extensions of the above methods known to persons having ordinary skill in the art.

Labeling of a nucleic acid may be achieved by replicating the nucleic acid in the presence of a modified nucleotide analog having a label, which leads to the incorporation of that label into the newly generated nucleic acid. The labeling process can also be achieved by incorporating a nucleotide analog with a functional group that can be used to covalently attach an energy accepting moiety in a secondary labeling step. Such replication can be accomplished by whole genome amplification (Zhang, L. et al., *Proc. Natl. Acad. Sci. USA* 89 (1992): 5847) or strand displacement amplification such as rolling circle amplification, nick translation, transcription, reverse transcription, primer extension and polymerase chain reaction (PCR), degenerate oligonucleotide primer PCR (DOP-PCR) (Telenius, H. et al., *Genomics* 13 (1992): 718-725) or combinations of the above methods.

A label may comprise a reactive group such as a nucleophile (amines, thiols etc.). Such nucleophiles, which are not present in natural nucleic acids, can then be used to attach fluorescent labels via amine or thiol reactive chemistry such as NHS esters, maleimides, epoxy rings, isocyanates etc. Such nucleophile reactive fluorescent dyes (i.e. NHS-dyes) are readily commercially available from different sources. An advantage of labeling a nucleic acid with small nucleophiles lies in the high efficiency of incorporation of such labeled nucleotides when a "labeling by synthesis" approach is used. Bulky fluorescently labeled nucleic acid building blocks may be poorly incorporated by polymerases due to sterical hindrance of the labels during the polymerization process into newly synthesized DNA.

DNA can be directly chemically modified without polymerase mediated incorporation of labeled nucleotides. One example of a modification includes cis-platinum containing dyes that modify Guanine bases at their N7 position (Hoevel, T. et al., *Bio Techniques* 27 (1999): 1064-1067). Another example includes the modifying of pyrimidines with hydroxylamine at the C6 position which leads to 6-hydroxylamino derivatives. The resulting amine groups can be further modified with amine reactive dyes (e.g. NHS-Cy5).

A nucleic acid molecule may be directly modified with N-Bromosuccinimide which upon reacting with the nucleic acid will result in 5-Bromocystein, 8-Bromoadenine and 8-Bromoguanine. The modified nucleotides can be further reacted with di-amine nucleophiles. The remaining nucleophile can then be reacted with an amine reactive dye (e.g.

NHS-dye) (Hermanson G. in *Bioconjugate Techniques*, Academic Press 1996, ISBN 978-0-12-342336-8).

A combination of 1, 2, 3 or 4 nucleotides in a nucleic acid strand may be exchanged with their labeled counterpart. The various combinations of labeled nucleotides can be sequenced in parallel, e.g., labeling a source nucleic acid or DNA with combinations of 2 labeled nucleotides in addition to the four single labeled samples, which will result in a total of 10 differently labeled sample nucleic acid molecules or DNAs (G, A, T, C, GA, GT, GC, AT, AC, TC). The resulting sequence pattern may allow for a more accurate sequence alignment due to overlapping nucleotide positions in the redundant sequence read-out.

A method for sequencing a polymer, such as a nucleic acid molecule includes providing a nanopore or pore protein (or a synthetic pore) inserted in a membrane or membrane like structure or other substrate. The base or other portion of the pore may be modified with one or more pore labels. The base may refer to the Trans side of the pore. Optionally, the Cis and/or Trans side of the pore may be modified with one or more pore labels. Nucleic acid polymers to be analyzed or sequenced may be used as a template for producing a labeled version of the nucleic acid polymer, in which one of the four nucleotides or up to all four nucleotides in the resulting polymer is/are replaced with the nucleotide's labeled analogue(s). An electric field is applied to the nanopore which forces the labeled nucleic acid polymer through the nanopore, while an external monochromatic or other light source may be used to illuminate the nanopore, thereby exciting the pore label. As, after or before labeled nucleotides of the nucleic acid pass through, exit or enter the nanopore, energy is transferred from the pore label to a nucleotide label, which results in emission of lower energy radiation. The nucleotide label radiation is then detected by a confocal microscope setup or other optical detection system or light microscopy system capable of single molecule detection known to people having ordinary skill in the art. Examples of such detection systems include but are not limited to confocal microscopy, epifluorescent microscopy and total internal reflection fluorescent (TIRF) microscopy. Other polymers (e.g., proteins and polymers other than nucleic acids) having labeled monomers may also be sequenced according to the methods described herein.

Energy may be transferred from a pore or nanopore donor label (e.g., a Quantum Dot) to an acceptor label on a polymer (e.g., a nucleic acid) when an acceptor label of an acceptor labeled monomer (e.g., nucleotide) of the polymer interacts with the donor label as, after or before the labeled monomer exits, enters or passes through a nanopore. For example, the donor label may be positioned on or attached to the nanopore on the cis or trans side or surface of the nanopore such that the interaction or energy transfer between the donor label and acceptor label does not take place until the labeled monomer exits the nanopore and comes into the vicinity or proximity of the donor label outside of the nanopore channel or opening. As a result, interaction between the labels, energy transfer from the donor label to the acceptor label, emission of energy from the acceptor label and/or measurement or detection of an emission of energy from the acceptor label may take place outside of the passage, channel or opening running through the nanopore, e.g., within a cis or trans chamber on the cis or trans sides of a nanopore. The measurement or detection of the energy emitted from the acceptor label of a monomer may be utilized to identify the monomer.

The nanopore label may be positioned outside of the passage, channel or opening of the nanopore such that the label may be visible or exposed to facilitate excitation or illumination of the label. The interaction and energy transfer between a donor label and accepter label and the emission of energy from the acceptor label as a result of the energy transfer may take place outside of the passage, channel or opening of the nanopore. This may facilitate ease and accuracy of the detection or measurement of energy or light emission from the acceptor label, e.g., via an optical detection or measurement device. The donor and acceptor label interaction may take place within a channel of a nanopore and a donor label could be positioned within the channel of a nanopore.

A donor label may be attached in various manners and/or at various sites on a nanopore. For example, a donor label may be directly or indirectly attached or connected to a portion or unit of the nanopore. Alternatively, a donor label may be positioned adjacent to a nanopore.

Each acceptor labeled monomer (e.g., nucleotide) of a polymer (e.g., nucleic acid) can interact sequentially with a donor label positioned on or next to or attached directly or indirectly to a nanopore or channel through which the polymer is translocated. The interaction between the donor and acceptor labels may take place outside of the nanopore channel or opening, e.g., after the acceptor labeled monomer exits the nanopore or before the monomer enters the nanopore. The interaction may take place within or partially within the nanopore channel or opening, e.g., while the acceptor labeled monomer passes through, enters or exits the nanopore.

When one of the four nucleotides of a nucleic acid is labeled, the time dependent signal arising from the single nucleotide label emission is converted into a sequence corresponding to the positions of the labeled nucleotide in the nucleic acid sequence. The process is then repeated for each of the four nucleotides in separate samples and the four partial sequences are then aligned to assemble an entire nucleic acid sequence.

When multi-color labeled nucleic acid (DNA) sequences are analyzed, the energy transfer from one or more donor labels to each of the four distinct acceptor labels that may exist on a nucleic acid molecule may result in light emission at four distinct wavelengths or colors (each associated with one of the four nucleotides) which allows for a direct sequence read-out.

During sequencing of a nucleic acid molecule, the energy transfer signal may be generated with sufficient intensity that a sensitive detection system can accumulate sufficient signal within the transit time of a single nucleotide through the nanopore to distinguish a labeled nucleotide from an unlabeled nucleotide. Therefore, the pore label may be stable, have a high absorption cross-section, a short excited state lifetime, and/or temporally homogeneous excitation and energy transfer properties. The nucleotide label may be capable of emitting and absorbing sufficient radiation to be detected during the transit time of the nucleotide through the pore. The product of the energy transfer cross-section, emission rate, and quantum yield of emission may yield sufficient radiation intensity for detection within the single nucleotide transit time. A nucleotide label may also be sufficiently stable to emit the required radiation intensity and without transience in radiation emission.

The excitation radiation source may be of high enough intensity that when focused to the diffraction limit on the nanopore, the radiation flux is sufficient to saturate the pore label. The detection system may filter out excitation radiation and pore label emission while capturing nucleic acid label emission during pore transit with sufficient signal-to-noise ratio (S/N) to distinguish a labeled nucleotide from an unlabeled nucleotide with high certainty. The collected nucleic acid label radiation may be counted over an integration time equivalent to the single nucleotide pore transit time.

A software signal analysis algorithm may then be utilized which converts the binned radiation intensity signal to a sequence corresponding to a particular nucleotide. Combination and alignment of four individual nucleotide sequences (where one of the four nucleotides in each sequence is labeled) allows construction of the complete nucleic acid sequence via a specifically designed computer algorithm.

A system for sequencing one or more biological polymers, e.g., nucleic acid molecules, may include a fixture or pore holder. The pore holder may include a nanopore membrane assembly wherein one or more nanopores span a lipid bilayer membrane. The nanopore membrane assembly has a Cis (−) side and a Trans (+) side. One or more labels may be attached to the nanopores. Alternatively, a label may be attached to a portion of the membrane or substrate through which the nanopore spans or to a linker or other molecule attached to the membrane, substrate or nanopore. An aqueous buffer solution is provided which surrounds the nanopore membrane assembly. The pore holder may contain two electrodes. A negative electrode or terminal may be positioned on the Cis side of the nanopore membrane assembly and a positive electrode or terminal may be positioned on the Trans side of the nanopore membrane assembly.

A flow of fluid or solution is provided on the side of the nanopore where the translocated polymer or nucleic acid exits after translocation through the nanopore. The flow may be continuous or constant such that the fluid or solution does not remain static for an extended period of time. The fluid flow or motion helps move or transfer translocated polymers away from the nanopore channel such the translocated polymers do not linger or accumulated near the nanopore channel exit or opening and cause fluorescent background or noise which could disrupt or prevent an accurate reading, measurement or detection of the energy emitted by a polymer acceptor label. Translocated polymers may include labels that were not fully exhausted, i.e. haven't reached their fluorescent lifetime and are still able to emit light. Such labels could interfere with the energy transfer between donor labels and subsequent monomer labels or emit energy that may interfere with the emission from other labels and disrupt an accurate reading or detection of energy from a labeled monomer.

One or more polymers, e.g., nucleic acid polymers or molecules, to be analyzed may also be provided. A polymer or nucleic acid polymer or molecule may include one or more labels, e.g., one or more monomers or nucleotides of the polymer may be labeled. A nucleic acid molecule may be loaded into a port positioned on the Cis side of then nanopore membrane assembly. The membrane segregates the nucleic acids to be analyzed to the Cis side of the nanopore membrane assembly. An energy source for exciting the nanopore label is provided, e.g., an illumination source. An electric field may be applied to or by the electrodes to force the labeled nucleic acid to translocate through the nanopore into the Cis side and out of the Trans side of the nanopore, from the Cis to the Trans side of the membrane, e.g., in a single file (Kasianowicz, J. J. et al., *Proc. Natl. Acad. Sci USA* 93 (1996): 13770-13773). Optionally, an electrical field may be applied utilizing other mechanisms to force the labeled nucleic acid to translocate through the nanopore. When a nucleic acid molecule is translocated through the nanopore and a labeled nucleotide comes into close proximity with the nanopore label, e.g., upon or after exiting the nanopore, energy is transferred from the excited nanopore label to a nucleotide label. A detector or detection system, e.g., optical detection system, for detecting or measuring energy emitted from the nucleotide label as a result of the transfer of energy from the nanopore label to the nucleotide label may also be provided.

The pore may be labeled with one or more donor labels in the form of quantum dots, metal nanoparticles, nano diamonds or fluorophores. The pore may be illuminated by monochromatic laser radiation. The monochromatic laser radiation may be focused to a diffraction limited spot exciting the quantum dot pore labels. As the labeled nucleic acid (e.g., labeled with an acceptor label in the form of a fluorophore) is translocated through the nanopore, the pore donor label (also "pore label" or "donor label") and a nucleotide acceptor label come into close proximity with one another and participate in a FRET (Förster resonance energy transfer) energy exchange interaction between the pore donor label and nucleic acid acceptor label (Ha, T. et al., *Proc. Natl. Acad. Sci. USA* 93 (1996): 6264-6268).

FRET is a non-radiative dipole-dipole energy transfer mechanism from a donor to acceptor fluorophore. The efficiency of FRET may be dependent upon the distance between donor and acceptor as well as the properties of the fluorophores (Stryer, L., Annu Rev Biochem. 47 (1978): 819-846).

A fluorophore may be any construct that is capable of absorbing light of a given energy and re-emitting that light at a different energy. Fluorophores include, e.g., organic molecules, rare-earth ions, metal nanoparticles, nanodiamonds and semiconductor quantum dots.

FIG. 2A shows one variation of a FRET interaction between a pore donor label 26 on a synthetic nanopore 22 and a nucleic acid acceptor label 28 on a nucleic acid 27 (e.g., a single or double stranded nucleic acid), which is being translocated through the synthetic nanopore 22. The synthetic nanopore 22 is positioned in a substrate 24. FRET is a non-radiative dipole-dipole energy transfer mechanism from a donor label 26 to an acceptor label 28 (e.g., a fluorophore). The efficiency of the energy transfer is, among other variables, dependent on the physical distance between acceptor label 28 and the donor label.

The nucleic acid acceptor label 28 positioned on a nucleotide of the nucleic acid moves into close proximity with an excited nanopore donor label 26, e.g., as or after the label 28 or labeled nucleotide exits the nanopore 22, and gets excited via FRET (indicated by the arrow A showing energy transfer from the pore label 26 to the nucleic acid label 28). As a result, the nucleic acid label 28 emits light of a specific wavelength, which can then be detected with the appropriate optical equipment or detection system in order to identify the labeled nucleotide corresponding to or associated with the detected wavelength of emitted light.

FIG. 2B shows translocation of the labeled nucleic acid 27 at a point in time where no FRET is taking place (due to the acceptor and donor labels not being in close enough proximity to each other). This is indicated by the lack of any arrows showing energy transfer between a pore label 26 and a nucleic acid label 28.

Figure 2C:
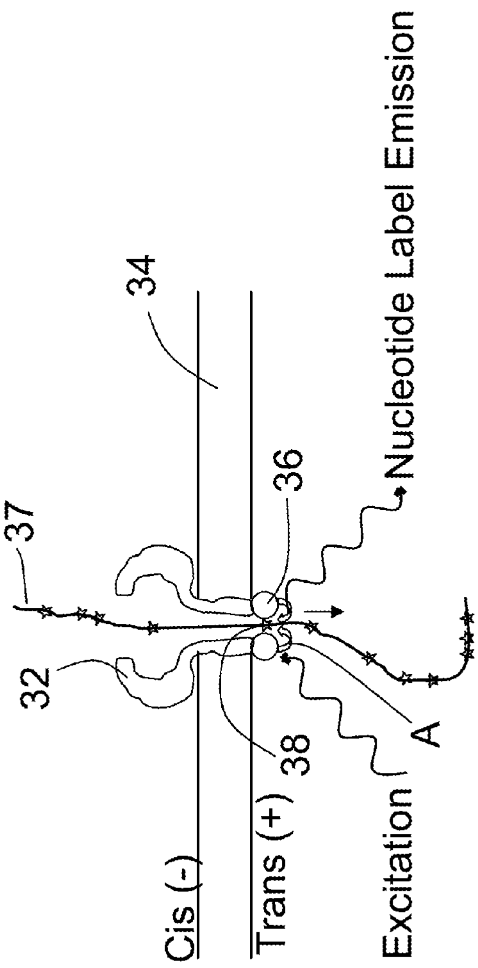
FIG. 2C illustrates one variation of a FRET interaction between a pore label on a protein nanopore and a nucleic acid label on a nucleic acid which is being translocated through the protein nanopore.

FIG. 2C shows one variation of a FRET interaction between a pore donor label 36 on a proteinaceous or protein nanopore 32 and a nucleic acid acceptor label 38 on a nucleic acid 37 (e.g., a single or double stranded nucleic acid), which is being translocated through the protein pore or nanopore 32. The pore protein 32 is positioned in a lipid bilayer 34. The nucleic acid acceptor label 38 positioned on a nucleotide of the nucleic acid moves into close proximity with an excited nanopore donor label 36, e.g., as or after the label 38 or labeled nucleotide exits the nanopore 32, and gets excited via FRET (indicated by the arrow A showing energy transfer from the pore label 36 to the nucleic acid label 38). As a result, the nucleic acid label 38 emits light of a specific wavelength, which can be detected with the appropriate optical equipment or detection system in order to identify the labeled nucleotide corresponding to or associated with the detected wavelength of emitted light.

Figure 2D:
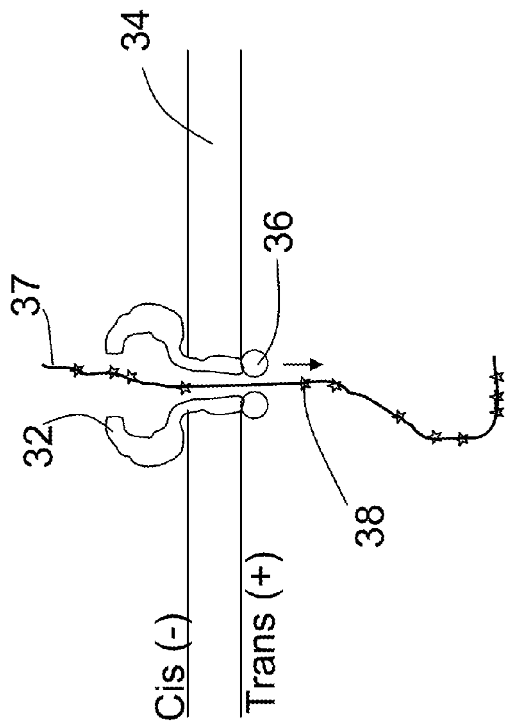
FIG. 2D illustrates translocation of a labeled nucleic acid through a protein nanopore at a point in time where no FRET is taking place.

FIG. 2D shows translocation of the labeled nucleic acid 37 at a point in time where no FRET is taking place (due to the labels not being in close enough proximity to each other). This is indicated by the lack of arrows showing energy transfer between a pore donor label 36 and a nucleic acid label 38.

Three equations are also shown below: Equation (1) gives the Förster radius which is defined as the distance that energy transfer efficiency from donor to acceptor is 50%. The Förster distance depends on the refractive index ($n_D$), quantum yield of the donor ($Q_D$), spatial orientation (K) and the spectral overlap of the acceptor and donor spectrum (I). $N_A$ is the Avogadro number with $N_A$=6.022×$10^{23}$ $mol^{-1}$ (see equation below). Equation (2) describes the overlap integral for the donor and acceptor emission and absorption spectra respectively; Equation (3) shows the FRET energy transfer efficiency as a function of distance between the acceptor and donor pair. The equations demonstrate that spectral overlap controls the Förster radius, which determines the energy transfer efficiency for a given distance between the FRET pair. Therefore by tuning the emission wavelength of the donor, the distance at which energy transfer occurs can be controlled.

$$R_0\left(\frac{9000(\ln 10)\kappa_p^2 Q_D}{N_A 128\pi^5 n_D^4} I\right)^{1/6} \tag{1}$$

$$I = \int J(\lambda)d\lambda = \int PL_{D\text{-}corr}(\lambda) \times \lambda^4 \times \varepsilon_A(\lambda)d\lambda \tag{2}$$

$$E = \frac{k_{DA}}{k_{DA} + \tau_D^{-1}} = \frac{R_0^6}{R_0^6 + r^6} \tag{3}$$

With respect to Quantum dots, due to the size dependent optical properties of quantum dots, the donor emission wavelength may be adjusted. This allows the spectral overlap between donor emission and acceptor absorption to be adjusted so that the Förster radius for the FRET pair may be controlled. The emission spectrum for Quantum dots is narrow, (e.g., 25 nm Full width-half maximum—FWHM—is typical for individual quantum dots) and the emission wavelength is adjustable by size, enabling control over the donor label-acceptor label interaction distance by changing the size of the quantum dots. Another important attribute of quantum dots is their broad absorption spectrum, which allows them to be excited at energies that do not directly excite the acceptor label. The properties allow quantum dots of the properly chosen size to be used to efficiently transfer energy with sufficient resolution to excite individual labeled nucleotides as, after or before the labeled nucleotides travel through a donor labeled pore.

Following a FRET energy transfer, the pore donor label may return to the electronic ground state and the nucleotide acceptor label can re-emit radiation at a lower energy. Where fluorophore labeled nucleotides are utilized, energy transferred from the fluorophore acceptor label results in emitted photons of the acceptor label. The emitted photons of the acceptor label may exhibit lower energy than the pore label emission. The detection system for fluorescent nucleotide labels may be designed to collect the maximum number of photons at the acceptor label emission wavelength while filtering out emission from a donor label (e.g., quantum dot donors) and laser excitation. The detection system counts photons from the labeled monomers as a function of time. Photon counts are binned into time intervals corresponding to the translocation time of, for instance, a monomer comprising a single nucleotide in a nucleic acid polymer crossing the nanopore. Spikes in photon counts correspond to labeled nucleotides translocating across the pore. To sequence the nucleic acid, sequence information for a given nucleotide is determined by the pattern of spikes in photon counts as a function of time. An increase in photon counts is interpreted as a labeled nucleotide.

Translocation of nucleic acid polymers through the nanopore may be monitored by current measurements arising from the flow of ions through the nanopore. Translocating nucleic acids partially block the ionic flux through the pore resulting in a measurable drop in current. Thus, detection of a current drop represents detection of a nucleic acid entering the pore, and recovery of the current to the original value represents detection of a nucleic acid exiting the pore.

Figure 3:
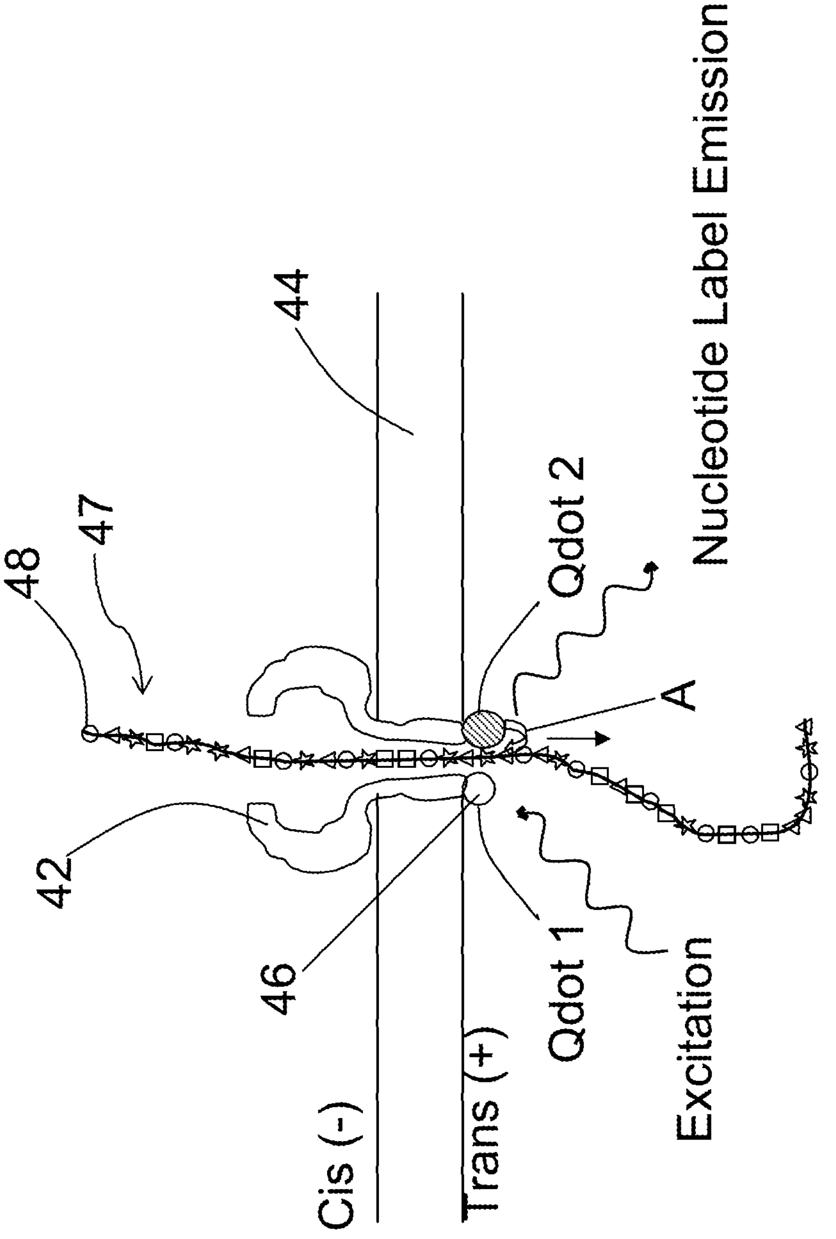
FIG. 3 illustrates one variation of a multicolor FRET interaction between the donor labels (Quantum dots) of a protein nanopore and the acceptor labels of a nucleic acid. Each shape on the nucleic acid represents a specific acceptor label, where each label has a distinct emission spectra associated with a specific nucleotide such that each label emits light at a specific wavelength associated with a specific nucleotide.

As mentioned supra, a multicolor FRET interaction is utilized to sequence a molecule such a nucleic acid. FIG. 3 shows one variation of a multicolor FRET interaction between one or more donor labels 46 (e.g., Quantum dots) of a protein nanopore 42 (optionally, a synthetic nanopore may be utilized) and one or more acceptor labels 48 of a nucleic acid molecule 47 (e.g., a single or double stranded nucleic acid). Each shape on the nucleic acid 47 represents a specific type of acceptor label labeling a nucleotide, where each label has a distinct emission spectra associated with or corresponding to a specific nucleotide such that each label emits light at a specific wavelength or color associated with a specific nucleotide.

In FIG. 3, each of the four shapes (triangle, rectangle, star, circle) represents a specific acceptor label 48, each label having a distinct emission spectra (e.g., 4 different emission spectra). Each of the acceptor labels 48 can form a FRET pair with a corresponding donor label or quantum dot 46 attached to the base of the nanopore. Qdot1 and Qdot2 represent two different Quantum dots as donor labels 46 that form specific FRET pairs with a nucleic acid acceptor label 48. The Quantum dot donor labels 46 are in an excited state and depending on the particular acceptor label 48 that comes in proximity to the Quantum dots during, after or before a labeled nucleotide translocation through the nanopore 42, an energy transfer (arrow A) from the donor label 46 to the nucleotide acceptor label 48 takes place, resulting in a nucleotide label 48 energy emission. As a result, each nucleotide may emit light at a specific wavelength or color (due to the distinct emission spectrum of the nucleotide's label), which can be detected (e.g., by optical detection) and used to identify or deduce the nucleotide sequence of the nucleic acid 47 and the nucleic acid 47 sequence.

Different pore labels exhibiting different spectral absorption maxima may be attached to a single pore. The nucleic acid may be modified with corresponding acceptor dye labeled nucleotides where each donor label forms FRET pairs with one acceptor labeled nucleotide (i.e. multi-color FRET). Each of the four nucleotides may contain a specific acceptor label which gets excited by one or more of the pore donor labels. The base of the pore may be illuminated with different color light sources to accommodate the excitation of the different donor labels. Alternatively, e.g., where Quantum dots are used as donor labels, the broad absorption spectra characteristic of Quantum dots may allow for a single wavelength light source to sufficiently illuminate/excitate the different donor labels which exhibit different spectral absorption maxima.

A single pore donor label (e.g., a single Quantum dot) may be suitable for exciting one nucleic acid acceptor label. For example, four different pore donor labels may be provided where each donor label can excite one of four different nucleic acid acceptor labels resulting in the emission of four distinct wavelengths. A single pore donor label (e.g., a single Quantum dot) may be suitable for exciting two or more nucleic acid acceptor labels that have similar absorption spectra overlapping with the donor label emission spectrum and show different emission spectra (i.e. different Stoke's shifts), where each acceptor label emits light at a different wavelength after excitation by the single donor label. Two different pore donor labels (e.g., two Quantum dots having different emission or absorption spectra) may be suitable for exciting four nucleic acid acceptor labels having different emission or excitation spectra, which each emit light at different wavelengths. One donor label or Quantum dot may be capable of exciting two of the nucleic acid acceptor labels resulting in their emission of light at different wavelengths, and the other Quantum dot may be capable of exciting the other two nucleic acid acceptor labels resulting in their emission of light at different wavelengths. The above arrangements provide clean and distinct wavelength emissions from each nucleic acid acceptor label for accurate detection.

A nanopore may include one or more monomers or attachment points, e.g., about 7 attachment points, one on each of the seven monomers making up a particular protein nanopore, such as alpha-hemolysin. One or more different donor labels, e.g., Quantum dots, may attach one to each of the attachment points, e.g., a nanopore may have up to seven different Quantum dots attached thereto. A single donor label or Quantum dot may be used to excite all four different nucleic acid acceptor labels resulting in a common wavelength emission suitable for detecting a molecule or detecting the presence of a molecule, e.g., in a biosensor application.

For accumulation of the raw signal data where a multicolor FRET interaction is utilized, the emission wavelength of the four different acceptor labels may be filtered and recorded as a function of time and emission wavelength, which results in a direct read-out of sequence information.

As mentioned supra, a nucleic acid sample may be divided into four parts to sequence the nucleic acid. The four nucleic acid or DNA samples may be used as a template to synthesize a labeled complementary nucleic acid polymer. Each of the four nucleic acid samples may be converted in a way such that one of the four nucleotide types (Guanine, Adenine, Cytosine or Thymine) are replaced with the nucleotide's labeled counterpart or otherwise labeled by attaching a label to a respective nucleotide. The same label may be used for each nucleotide or optionally, different labels may be used. The remaining nucleotides are the naturally occurring nucleic acid building blocks. Optionally, two, three or each nucleotide of a nucleic acid may be replaced with a nucleotide carrying a distinct acceptor label.

To perform the sequence read-out where a single nucleotide label is utilized with the target nucleic acid split into four samples, each having one nucleotide labeled with the same, or optionally, a different acceptor label, a specially designed algorithm may be utilized which (i) corrects, (ii) defines, and (iii) aligns the four partial sequences into one master sequence. Each partial sequence displays the relative position of one of the four nucleotides in the context of the whole genome sequence, thus, four sequencing reactions may be required to determine the position of each nucleotide.

The algorithm may correct for missing bases due to inefficient labeling of the nucleic acid. One type of nucleotide in a DNA molecule can be completely substituted with the nucleotide's fluorescent counterpart. Various inefficiencies in labeling may result in less than 100% coverage from this substitution. Fluorescently labeled nucleotides usually come at a purity of around 99%, i.e., approximately 1% of the nucleotides do not carry a label. Consequently, even at a 100% incorporation of modified nucleotides, 1% of the nucleotides may be unlabeled and may not be detectable by nanopore transfer sequencing.

One solution to this problem is a redundant coverage of the nucleic acid to be sequenced. Each sequence may be read multiple times, e.g., at least 50 times per sequencing reaction (i.e. a 50 fold redundancy). Thus, the algorithm will compare the 50 sequences which will allow a statistically sound determination of each nucleotide call.

The algorithm may define the relative position of the sequenced nucleotides in the template nucleic acid. For example, the time of the current blockage during the translocation process may be used to determine the relative position of the detected nucleotides. The relative position and the time of the occurrence of two signals may be monitored and used to determine the position of the nucleotides relative to each other. Optionally, a combination of the above methods may be used to determine the position of the nucleotides in the sequence.

The nucleic acid or DNA to be analyzed may be separated into four samples. Each sample will be used to exchange one form of nucleotide (A, G, T, or C) with the nucleotide's fluorescent counterpart. Four separate nanopore sequencing reactions may reveal the relative positions of the four nucleotides in the DNA sample through optical detection. A computer algorithm will then align the four sub-sequences into one master sequence. The same acceptor label capable of emitting light at a specific wavelength or color may be utilized in all four samples. Optionally, different labels having different wavelength emissions may be utilized.

Figure 4A:
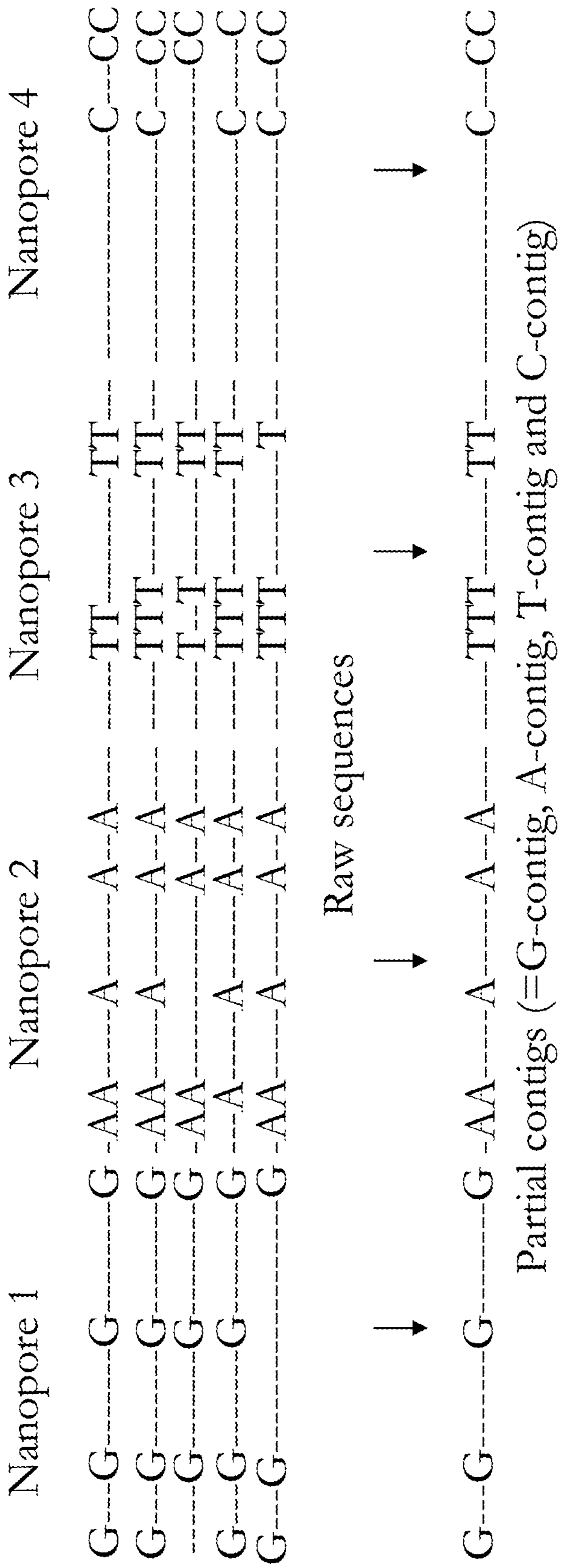
FIG. 4A illustrates partial contigs from nucleic acid sequencing utilizing a singly labeled nucleic acid.

For example, FIG. 4A shows partial contigs from nucleic acid sequencing utilizing a singly labeled nucleic acid. Four separate nanopore sequencing reactions take place. Each of the four separate nanopore sequencing reactions, which are created by the same type of nucleotide acceptor label, generates a sub-sequence that displays the relative position of one of the four nucleotides. A redundant coverage of each sequence may ensure statistical sound base calls and readouts. A computer algorithm may be utilized to deduce the four partial contig sequences which are the common denominators of the multiple covered sub-sequences (i.e. G-contig, A-contig, T-contig, and C-contig).

Figure 4B:
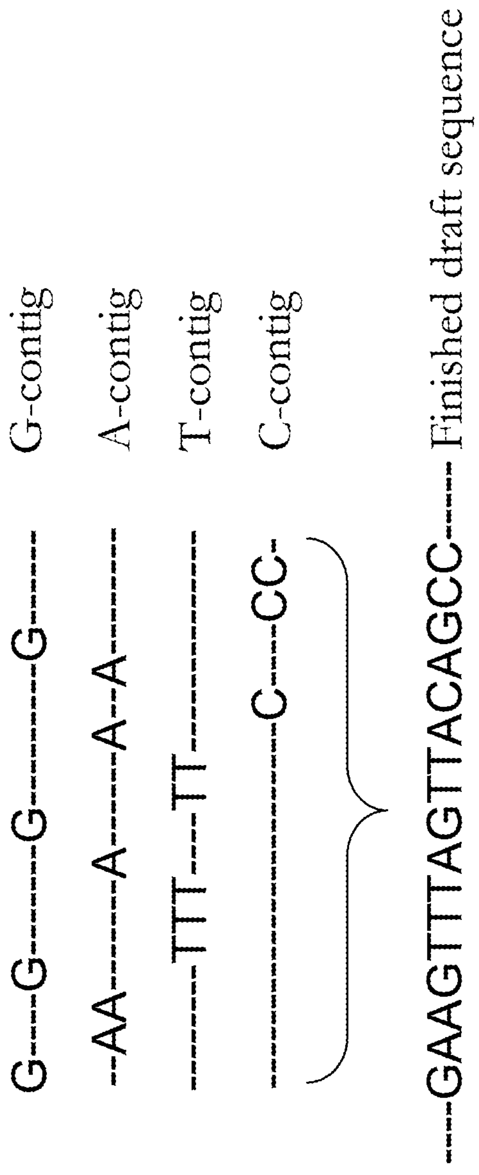
FIG. 4B illustrates how partial contig alignment may generate a first draft nucleic acid sequence (GAAGTTTAGTTACAGCC (SEQ ID NO: 1)).

FIG. 4B shows how partial contig alignment may generate a first draft nucleic acid sequence. For example, the second bioinformatic step involves alignment of the four contigs. Software searches for matching sequence stretches of the four contigs that complement each other. This step results in a finished draft sequence.

Optionally, both optical and electrical read-outs/detection may be utilized to sequence a nucleic acid. Electrical readouts may be utilized to measure the number of non-labeled nucleotides in a sequence to help assess the relative position of a detected labeled nucleotide on a nucleic acid sequence. The length of the nucleic acid can be calculated by measuring the change in current through the nanopore and the duration of that current change. The methods and systems described herein may utilize solely optical read-outs or optical detection of energy emission or light emission by a labeled monomer to identify and sequence the monomer and to sequence a polymer including the monomer. Optionally, a combination of optical and electrical readouts or detection may be used.

A nucleotide acceptor label may be in the form of a quencher which may quench the transferred energy. In the case of a quenching nucleotide label, radiation emission from the pore donor label will decrease when a labeled nucleotide is in proximity to the donor label. The detection system for quenching pore labels is designed to maximize the radiation collected from the pore labels, while filtering out laser excitation radiation. For a quenching label, a decrease in photon counts of the pore label, such as a quantum dot, is interpreted as a labeled nucleotide.

Figure 5A:
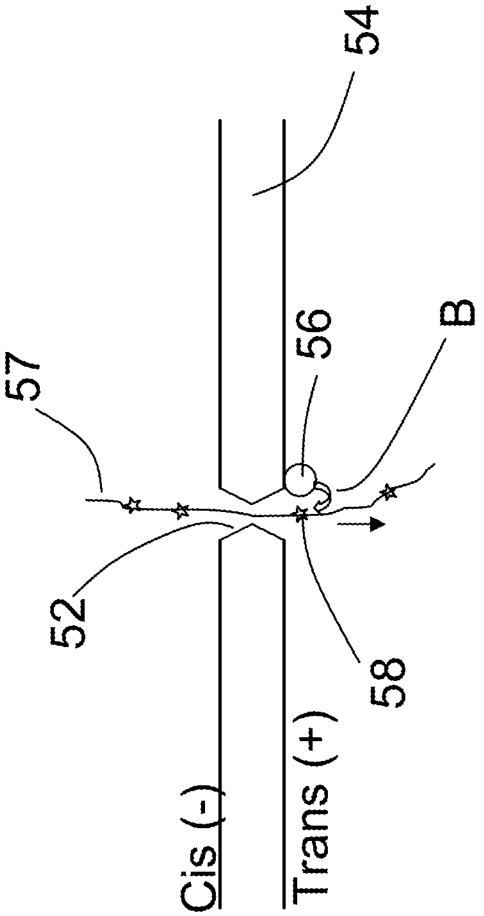
FIG. 5A illustrates one variation of a quenching interaction between a pore label on a synthetic nanopore and a nucleic acid label on a nucleic acid which is being translocated through the synthetic nanopore.

FIG. 5A shows one variation of a quenching interaction between a pore donor label 56 on a synthetic pore or nanopore 52 and a nucleic acid quenching label 58 on a nucleic acid 57 (e.g., a single or double stranded nucleic acid), which is being translocated through the synthetic nanopore 52. The synthetic nanopore 52 is positioned in a substrate 54, e.g., a solid substrate.

During a continuous or substantially continuous illumination of the pore label 56, the pore label 56 emits light at a certain wavelength which is detected with an appropriate optical or other detection system. The quenching label 58 positioned on a nucleotide of nucleic acid 57 comes in close proximity to the pore label 56, e.g., as or after the label 58 or labeled nucleotide exits the nanopore 52, and thereby quenches the pore label 56. The quenching label 58 acts by absorption of energy from the illuminated pore label 56 (which is indicated by arrow B) causing the photon emission from the pore label 56 to change. For example, the quenching may be detected by detecting a change, such as a decrease or diminishing, in the photons emitted by the nanopore label. A degree of photon emission change may be associated with or correspond to a single nucleotide of the nucleic acid molecule and as such, the nucleic acid molecule sequence may be deduced based on detecting the change in photon emission by the donor label caused by the quenching label.

Figure 5B:
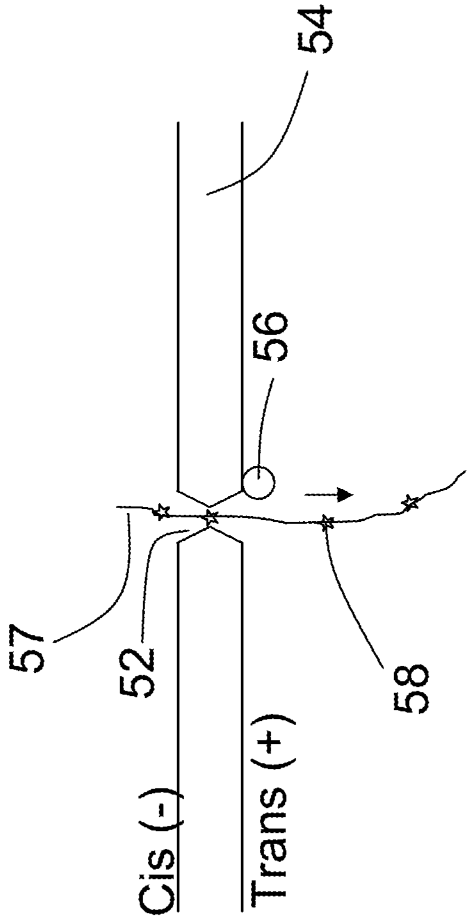
FIG. 5B illustrates translocation of the labeled nucleic acid through a synthetic nanopore at a point in time where no quenching is taking place.

FIG. 5B shows translocation of the labeled nucleic acid 57 at a point in time where no quenching is taking place (due to the labels not being in close enough proximity to each other). This is indicated by the lack of any arrows showing energy transfer between a pore label 56 and a nucleic acid label 58.

Figure 5C:
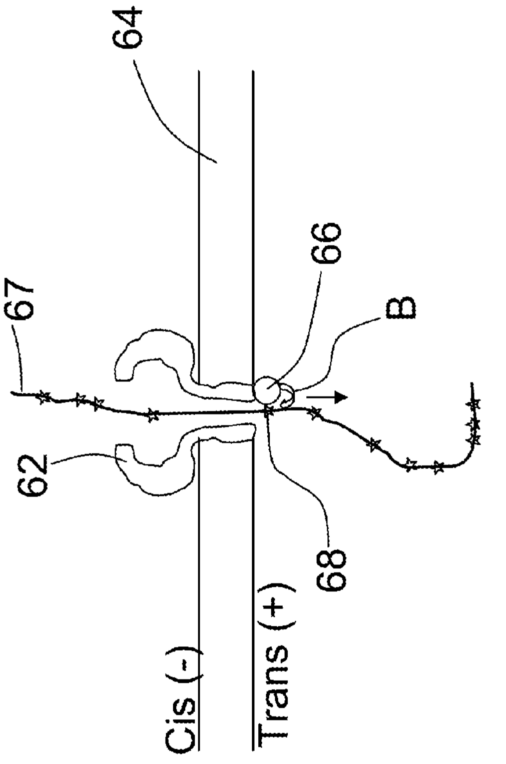
FIG. 5C illustrates one variation of a quenching interaction between a pore label on a protein nanopore and a nucleic acid label on a nucleic acid which is being translocated through the protein nanopore.

FIG. 5C shows one variation of a quenching interaction between a pore donor label 66 on a proteinaceous or protein pore or nanopore 62 and a nucleic acid quenching label 68 on a nucleic acid 67 (e.g., a single or double stranded nucleic acid), which is being translocated through the protein nanopore 62. The protein nanopore 62 is positioned in a lipid bilayer 64.

During a continuous illumination of the pore label 66 the pore label 66 emits light at a certain wavelength which is detected with an appropriate optical or other detection system. The quenching label 68 positioned on a nucleotide of nucleic acid 67 comes in close proximity to the pore label 66, e.g., as or after the label 68 or labeled nucleotide exits the nanopore 62, and thereby quenches the pore label 66 (which is indicated by arrow B). This quenching is detected by a decrease or sharp decrease in measured photons emitted from the nanopore label.

Figure 5D:
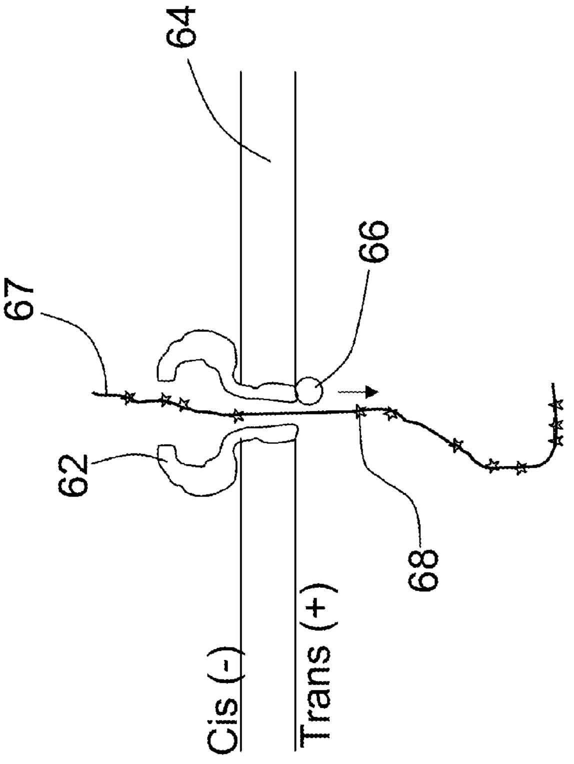
FIG. 5D illustrates translocation of a labeled nucleic acid through a protein nanopore at a point in time where no quenching is taking place.

FIG. 5D shows translocation of the labeled nucleic acid 67 at a point in time where no quenching is taking place (due to the labels not being in close enough proximity to each other). This is indicated by the lack of any arrows showing energy transfer between a pore label 66 and a nucleic acid label 68.

The energy transfer reaction, energy emission or pore label quenching as described above may take place as or before the label or labeled nucleotide enters the nanopore, e.g., on the cis side of the nanopore.

The labeling system may be designed to emit energy continuously without intermittency or rapid photobleaching of the fluorophores. For example, the buffer compartment of a pore holder may contain an oxygen depletion system that will remove dissolved Oxygen from the system via enzymatical, chemical or electrochemical means thereby reducing photobleaching of the fluorophore labeled nucleic acid.

An oxygen depletion system is a buffer solution containing components that selectively react with dissolved oxygen. Removing oxygen from the sequencing buffer solution helps prevent photobleaching of the fluorophore labels. An example of a composition of an oxygen depletion buffer is as follows: 10 mM tris-Cl, pH 8.0, 50 mM NaCl, 10 mM MgCl2, 1% (v/v) 2-mercaptoethanol, 4 mg/ml glucose, 0.1 mg/ml glucose oxidase, and 0.04 mg/ml catalase (Sabanayagam, C. R. et al., J. Chem. Phys. 123 (2005): 224708). The buffer is degassed by sonication before use to extend the buffer's useful lifetime by first removing oxygen mechanically. The buffer system then removes oxygen via the enzymatic oxidation of glucose by glucose oxidase.

The sequencing buffer may also contain components that prevent fluorescence intermittency, also referred to as "blinking," in one or both of the quantum dot labeled pores and fluorophore labeled nucleic acids. The phenomenon of blinking occurs when the excited fluorophore transitions to a non-radiative triplet state. Individual fluorophores may display fluorescence intermittency known as blinking in which the fluorophore transitions to and from the fluorophore's emitting and dark state. Blinking can interfere with certain aspects of the sequencing schemes. Blinking may be prevented or left alone. The triplet state is responsible for blinking in many organic fluorophores and that blinking can be suppressed with chemicals that quench the triplet state.

Molecules such as Trolox (6-hydroxy-2,5,7,8-tetramethylchroman-2-carboxylic acid) are effective in eliminating blinking for fluorophores or dyes such as Cy5 (Rasnik, I. et al., *Nat Methods* 11 (2006): 891-893). Certain Quantum dots may display blinking, however, CdTe quantum dots produced by aqueous synthesis in the presence of inercaptopropionic acid have recently been shown to emit continuously without blinking (He, H. et al., *Angew. Chem. Int. Ed.* 45 (2006): 7588-7591). CdTe quantum dots are ideally suited as labels to be utilized in the methods described herein, since they are water soluble with high quantum yield and can be directly conjugated through the terminal carboxylic acid groups of the mercaptopropionic acid ligands.

The labels may be made resistant to photobleaching and blinking. With an efficient oxygen depletion system, Cy5 fluorophores can undergo ~10ˆ5 cycles of excitation and emission before irreversible degradation. If the incident laser light is of high enough efficiency that excitation of the Cy5 fluorophore is saturated (re-excited immediately after emission) than the rate of photon emission is determined by the fluorescence lifetime of the Cy5 fluorophore. Since the Cy5 fluorophore has a lifetime on the order of 1 ns, and an assumed FRET efficiency of 10%, up to 10,000 photons can be emitted as the Cy5 labeled nucleotide transverses the nanopore. Microscopes used for single molecule detection are typically around 3% efficient in light collection. This can provide ~300 photons detected for a given label, which provides sufficiently high signal to noise ratio for single base detection.

A polymer or nucleic acid may be translocated through a nanopore having a suitable diameter (the diameter may vary, e.g., the diameter may be about 2 to 6 nm) at an approx. speed of 1,000 to 100,000 or 1,000 to 10,000 nucleotides per second. Each base of the nucleic acid may be fluorescently labeled with a distinct fluorophore. The base of the nanopore may be labeled with a quantum dot. When the nucleotide label comes in close proximity to the quantum dot, a non-radiative, quantum resonance energy transfer occurs which results in light emission of a specific wavelength form the nucleotide label.

Figure 6:
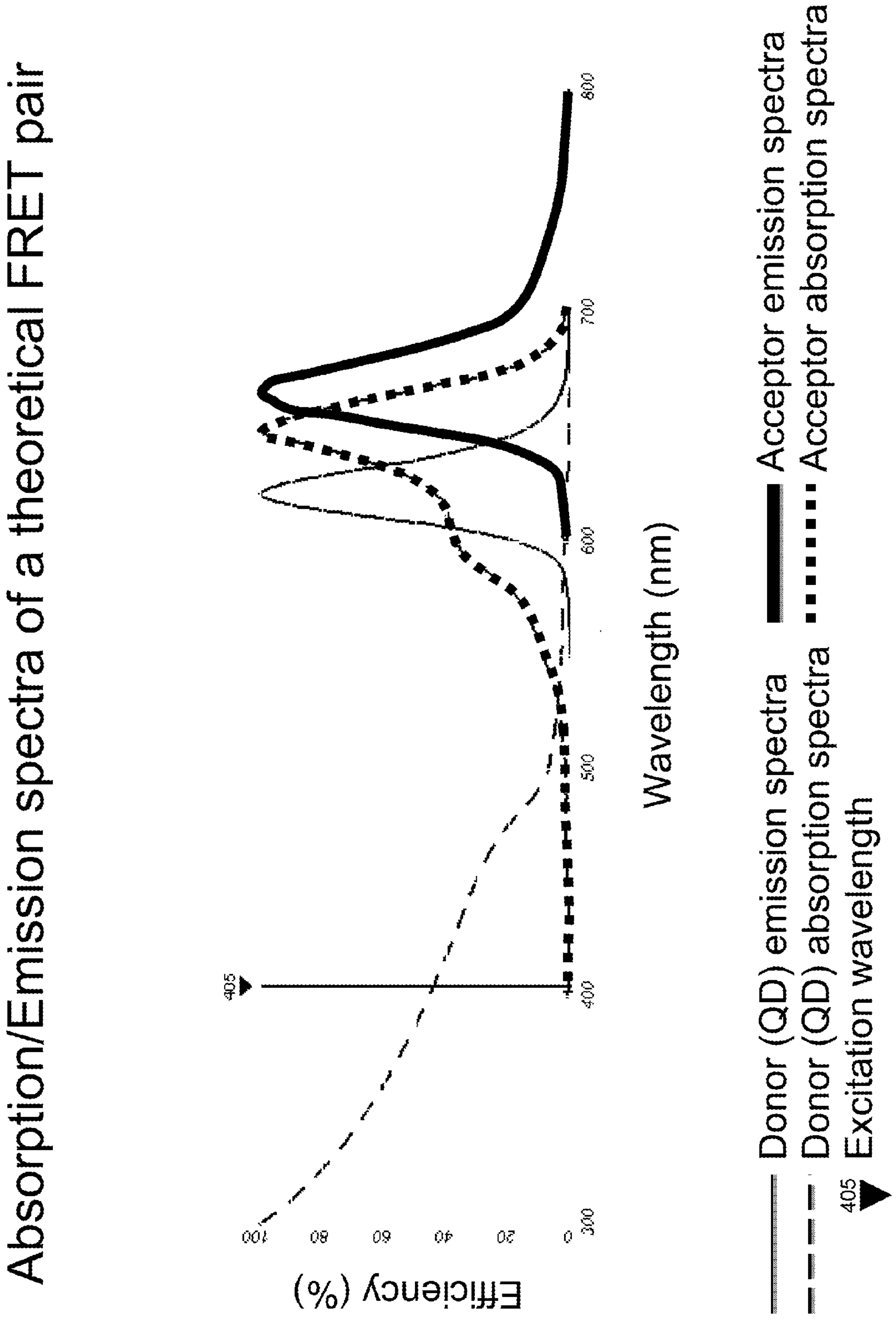
FIG. 6 shows an example of an absorption/emission spectra from a FRET pair containing a donor quantum dot and an acceptor fluorophore.

FIG. 6 shows an example of an absorption/emission spectra from a FRET pair containing a donor quantum dot and an acceptor fluorophore. The characteristic broad absorption peak (thin dashed line) of the quantum dot allows for a short excitation wavelength which doesn't interfere with the detection of the longer emission wavelength. The emission peak of the quantum dot (thin solid line) has a significant spectral overlap with the absorption peak of the acceptor fluorophore (thick dashed line). This overlap may result in an energy transfer from the quantum dot to the fluorophore which then emits photons of a specific wavelength (thick solid line). These fluorophore emitted photons are subsequently detected by an appropriate optical system. The efficiency of the energy transfer may be highly dependent on the distance between the donor and acceptor, with a 50% efficiency at the so called Foerster radius.

Sequencing may be performed by utilizing one or more pores or nanopores simultaneously. For example, a plurality of nanopores may be positioned in parallel or in any configuration in one or more lipid bilayers or substrates in order to expedite the sequencing process and sequence many nucleic acid molecules or other biological polymers at the same time.

A plurality of pores may be configured on a rotatable disc or substrate. When donor labels or quantum dots become substantially or completely used, burned out or exhausted (i.e., they reached their fluorescent lifetime), the disc or substrate may be rotated, thereby rotating a fresh pore with fresh donor labels or quantum dots into place to receive nucleic acids and continue sequencing. The electrical field which pulls the nucleic acid through the pore may be turned off during rotation of the disc and then turned back on once a new pore is in position for sequencing. Optionally, the electric field may be left on continuously.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A system for sequencing a polymer comprising:

a nanopore substrate assembly having a donor labeled nanopore which spans a substrate, the nanopore substrate assembly having a negatively charged electrode on a cis side and a positively charged electrode on a trans side;

a polymer comprising monomers each having an acceptor label, wherein the polymer is negatively charged and is loaded on the cis side of the nanopore substrate assembly, so that the labeled monomers of the polymer are translocated in single file through the nanopore from the cis side to the trans side;

an energy source for exciting the nanopore donor label, wherein the nanopore donor label is configured to emit energy at a first wavelength in response to such excitation such that energy is transferred from the nanopore donor label to a monomer acceptor label whenever such monomer acceptor label exits the nanopore within an energy transfer distance of the nanopore donor label, each acceptor label being configured to emit energy at a second wavelength which is different from the first wavelength after such energy transfer;

and an optical detector for detecting the energy emitted from the monomer acceptor label as a result of the transfer of energy from the nanopore donor label to the monomer acceptor label, wherein the emitted energy is associated with a single monomer and facilitates the sequencing of the polymer.

2. The system of claim 1, wherein the donor label comprises one or more quantum dots and the acceptor label comprises one or more fluorophores.

3. The system of claim 1, wherein a plurality of nanopores are incorporated into the substrate in parallel, such that a plurality of polymers may be sequenced simultaneously.

4. The system of claim 1, wherein a plurality of nanopores are incorporated into a rotatable disc, such that the nanopores may be rotatably interchanged.

5. The method of claim 1, wherein the polymer is a nucleic acid and the monomer is a nucleotide.

6. The system of claim 1 wherein said enemy transfer distance is a Förster radius.

7. The system of claim 1 wherein said nanopore donor label is on said trans side of said nanopore substrate assembly.

8. A system for sequencing a polymer comprising:

a nanopore substrate assembly having a donor labeled nanopore which spans a substrate, the nanopore substrate assembly having a negatively charged side and a positively charged side;

an aqueous buffer solution surrounding the nanopore substrate assembly;

a negative electrical conductor positioned on the negatively charged side of the nanopore substrate assembly;

a positive electrical conductor positioned on the positively charged side of the nanopore substrate assembly;

a polymer comprising a monomer having an acceptor label, wherein the polymer is loaded into a port positioned on the negatively charged side of the nanopore substrate assembly;

an energy source for exciting the nanopore donor label, wherein the nanopore donor label is configured to emit energy at a first wavelength;

wherein the system is configured so that when an electric field is applied applied by the conductors to force the labeled polymer to translocate through the nanopore from the negatively charged side to the positively charged side in a single file, energy is transferred from the nanopore donor label to the monomer acceptor label after the labeled monomer passes through and exits the nanopore and comes in proximity to the nanopore donor label, wherein the energy transfer results in the monomer acceptor label emitting energy at a second wavelength which is different from the first wavelength; and an optical detector for detecting the energy emitted from the monomer acceptor label as a result of the transfer of energy from the nanopore donor label to the monomer acceptor label, wherein the emitted energy is associated with a single monomer and facilitates the sequencing of the polymer.

9. A method for sequencing a polymer comprising:

exciting a first label attached to a nanopore wherein the first label emits energy at a first wavelength;

translocating a polymer through the nanopore, wherein the polymer comprises monomers each labeled with a second label;

transferring energy from the excited first label to the second label of each monomer after the labeled monomer passes through and exits the nanopore, wherein the energy transfer results in the second label emitting energy at a second wavelength which is different from the first wavelength;

detecting the energy emitted by the second label as a result of the energy transfer, wherein the energy emitted by the second label is associated with a single monomer; and deducing the polymer sequence based on the detection of the emitted energy from the second labels and identification of the monomers.

10. The method of claim 9, wherein the labeled polymer is translocated through the nanopore by applying an electric field across the nanopore.

11. The method of claim 9, wherein the first label is a Quantum dot.

12. The method of claim 9, wherein the second label is a fluorophore.

13. The method of claim 9, wherein a plurality of first labels exhibiting different spectral emission maxima are attached to the nanopore and a plurality of second labels having distinct absorption/emission spectra each associated with a specific monomer are attached to the polymer, and wherein each first label and corresponding second label undergo a FRET (Förster Resonance Energy Transfer) interaction such that each second labeled monomer of the polymer emits a specific wavelength that is detected and used to sequence the polymer.

14. The method of claim 9, wherein detecting the energy emitted by the second label comprises optical detection of a specific wavelength emitted by the second label and associated with a specific nucleotide.

15. The method of claim 9, wherein the polymer is a nucleic acid and the monomer is a nucleotide and wherein said step of detecting generates time dependent signals associated with monomers.

16. The method of claim 15, wherein one of four nucleotide bases is labeled and the time dependent signal arising from a nucleotide label emission is converted into a nucleic acid sequence corresponding to positions of the labeled nucleotide in the nucleic acid sequence.

17. The method of claim 16, wherein the method is repeated for each of the four nucleotides in separate samples and four partial sequences are deduced and then aligned to assemble an entire nucleic acid sequence.

* * * * *